(12) United States Patent
Mor

(10) Patent No.: US 11,533,850 B2
(45) Date of Patent: Dec. 27, 2022

(54) SELF-PROPELLED ROBOTIC HARVESTER FOR SELECTIVE PICKING OF HIGH QUALITY AGRICULTURE ROW CROPS

(71) Applicant: Cottlab Ltd., Rehovot (IL)

(72) Inventor: Uzi Mor, Rehovot (IL)

(73) Assignee: ROBOTPICKS LTD., Rehovot (IL)

( * ) Notice: Subject to any disclaimer, the term of this patent is extended or adjusted under 35 U.S.C. 154(b) by 78 days.

(21) Appl. No.: 16/644,476

(22) PCT Filed: Sep. 3, 2018

(86) PCT No.: PCT/IL2018/050978
§ 371 (c)(1),
(2) Date: Mar. 4, 2020

(87) PCT Pub. No.: WO2019/049130
PCT Pub. Date: Mar. 14, 2019

(65) Prior Publication Data
US 2020/0281122 A1 Sep. 10, 2020

(51) Int. Cl.
*A01D 46/00* (2006.01)
*A01D 46/08* (2006.01)
(Continued)

(52) U.S. Cl.
CPC ......... *A01D 46/085* (2013.01); *A01D 46/084* (2013.01); *A01D 46/10* (2013.01);
(Continued)

(58) Field of Classification Search
CPC .... A01D 46/085; A01D 46/084; A01D 90/08; A01D 90/10; A01D 46/10; A01D 46/14;
(Continued)

(56) References Cited

U.S. PATENT DOCUMENTS

| 4,191,008 A | 3/1980 | Smith | |
| 4,452,134 A * | 6/1984 | Muse | A01D 46/08 100/100 |

(Continued)

FOREIGN PATENT DOCUMENTS

| CN | 201135036 Y | 10/2008 |
| CN | 201957458 U | 9/2011 |

(Continued)

OTHER PUBLICATIONS

Cotton Pickers' Lament, https://www.britishpathe.com/video/the-cotton-pickers-lament.

(Continued)

*Primary Examiner* — Lynn E Schwenning
(74) *Attorney, Agent, or Firm* — Bookoff McAndrews, PLLC

(57) ABSTRACT

The present invention relates to automatic and high throughput smart, robotic, autonomous or driver operated, self-propelled field crops harvester (SPFCH) device of row crops, characterized by the need of selecting harvesting ripen crop, during relative long period of time. Harvesting is done by one or more modular robotic harvesting arms hanged on modular booms. When harvesting orchards fruits the SPFCH comprise at least one hybrid robotic arms equipped with a grabbing hand aimed to grab one or more fruit of a an adjacent fruits and also cut its connecting stem, and arm transporting mechanism that gently collects the fruits and transport them to the SPFCH main accumulation area. When harvesting cotton, the SPFCH of the invention may further comprise vacuum sucking hoses and at least one ginning unit that gin the seed-cotton during harvesting and accumulate the seeds in a self-container, and the lint by bales processed, on board by self-press.

19 Claims, 28 Drawing Sheets

(51) Int. Cl.

| | | |
|---|---|---|
| *H02S 10/40* | (2014.01) | |
| *H02S 30/20* | (2014.01) | |
| *H02S 40/38* | (2014.01) | |
| *A01D 46/10* | (2006.01) | |
| *A01D 46/14* | (2006.01) | |
| *A01D 46/253* | (2006.01) | |
| *A01D 46/30* | (2006.01) | |
| *A01D 90/02* | (2006.01) | |
| *A01F 15/00* | (2006.01) | |
| *B25J 11/00* | (2006.01) | |
| *B25J 15/00* | (2006.01) | |
| *B25J 15/06* | (2006.01) | |
| *B60P 1/54* | (2006.01) | |
| *B65D 21/08* | (2006.01) | |
| *B65D 85/34* | (2006.01) | |
| *B65G 59/06* | (2006.01) | |
| *D01B 1/06* | (2006.01) | |
| *D01B 1/08* | (2006.01) | |
| *G01C 21/00* | (2006.01) | |
| *G01N 33/00* | (2006.01) | |
| *A01D 90/08* | (2006.01) | |
| *A01D 90/10* | (2006.01) | |
| *A01F 25/14* | (2006.01) | |
| *B25J 15/10* | (2006.01) | |

(52) U.S. Cl.
CPC ......... *A01D 46/14* (2013.01); *A01D 46/253* (2013.01); *A01D 46/30* (2013.01); *A01D 90/02* (2013.01); *A01D 90/08* (2013.01); *A01D 90/10* (2013.01); *A01F 15/00* (2013.01); *A01F 25/14* (2013.01); *B25J 11/0045* (2013.01); *B25J 15/0009* (2013.01); *B25J 15/0019* (2013.01); *B25J 15/0066* (2013.01); *B25J 15/0616* (2013.01); *B25J 15/10* (2013.01); *B60P 1/5423* (2013.01); *B65D 21/086* (2013.01); *B65D 85/34* (2013.01); *B65G 59/067* (2013.01); *D01B 1/06* (2013.01); *D01B 1/08* (2013.01); *G01C 21/00* (2013.01); *G01N 33/0098* (2013.01); *H02S 10/40* (2014.12); *H02S 30/20* (2014.12); *H02S 40/38* (2014.12); *B65G 2201/047* (2013.01)

(58) Field of Classification Search
CPC ...... A01D 46/253; A01D 46/30; A01D 90/02; A01F 25/14; B25J 15/0066; B25J 15/10; H02S 30/20; B60P 1/5423; D01B 1/06; D01B 1/08
See application file for complete search history.

(56) References Cited

U.S. PATENT DOCUMENTS

| | | | |
|---|---|---|---|
| 4,519,193 A | 5/1985 | Yoshida et al. | |
| 4,663,925 A * | 5/1987 | Terada | A01D 46/24 382/153 |
| 4,860,405 A * | 8/1989 | Eckley | D01B 1/02 19/0.27 |
| 5,768,869 A | 6/1998 | Welborn | |
| 7,500,343 B2 * | 3/2009 | Hsia | A01D 46/253 56/332 |
| 7,540,137 B2 * | 6/2009 | Gray | B25J 5/005 56/328.1 |
| 7,695,220 B2 | 4/2010 | Bryan, Jr. et al. | |
| 7,882,686 B2 | 2/2011 | Bryan, Jr. et al. | |
| 8,381,501 B2 * | 2/2013 | Koselka | A01D 46/30 56/10.2 A |
| 8,534,035 B1 | 9/2013 | Mitchell et al. | |
| 9,226,446 B2 | 1/2016 | Moore | |
| 9,475,189 B2 | 10/2016 | Kahani | |
| 10,542,671 B2 * | 1/2020 | D'Arrigo | A01D 45/263 |
| 10,674,666 B2 * | 6/2020 | Moore | A01D 46/005 |
| 2006/0213167 A1 | 9/2006 | Koselka et al. | |
| 2012/0009682 A1 | 1/2012 | Cho et al. | |
| 2019/0029178 A1 * | 1/2019 | Russel | A01D 46/30 |

FOREIGN PATENT DOCUMENTS

| | | |
|---|---|---|
| CN | 103503639 B | 1/2014 |
| CN | 203968702 U | 12/2014 |
| CN | 105706637 A | 6/2016 |
| DE | 102015111682 A | 2/2017 |

OTHER PUBLICATIONS

International Search Report for PCT/IL2018/050978, dated Jan. 16, 2019.

* cited by examiner

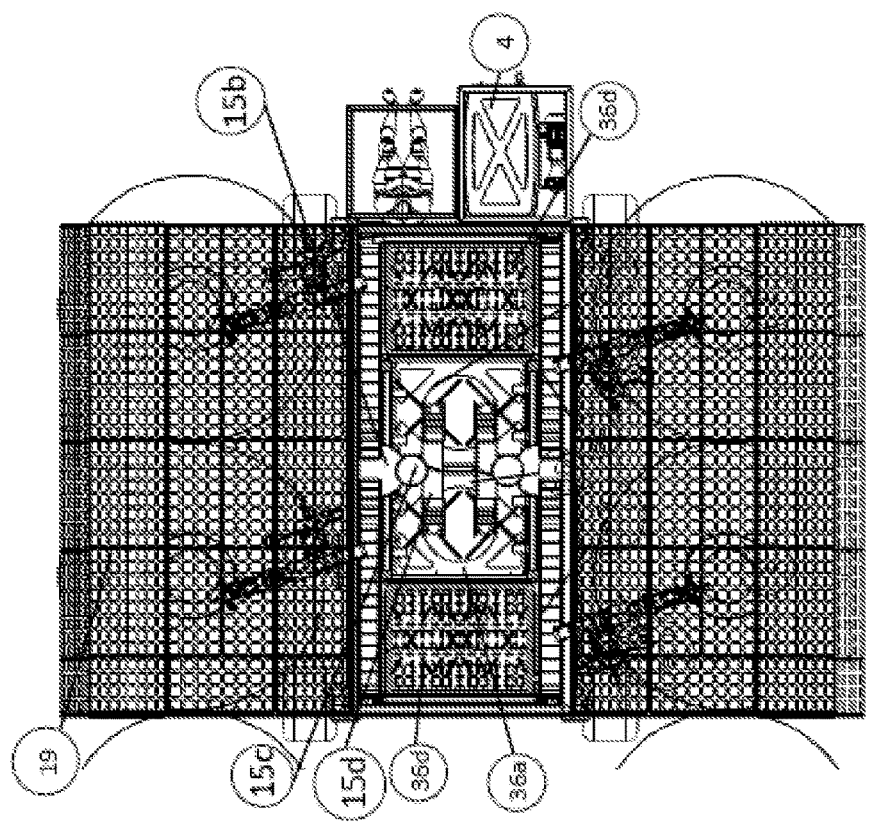
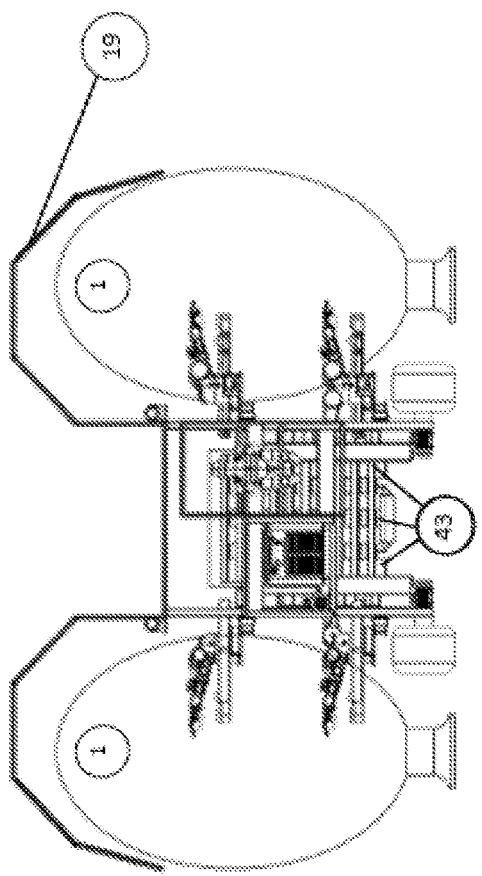
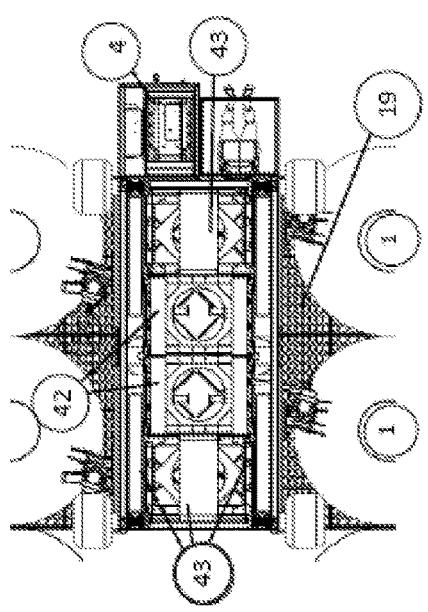
Fig. 3c
Fig. 3a
Fig. 3b

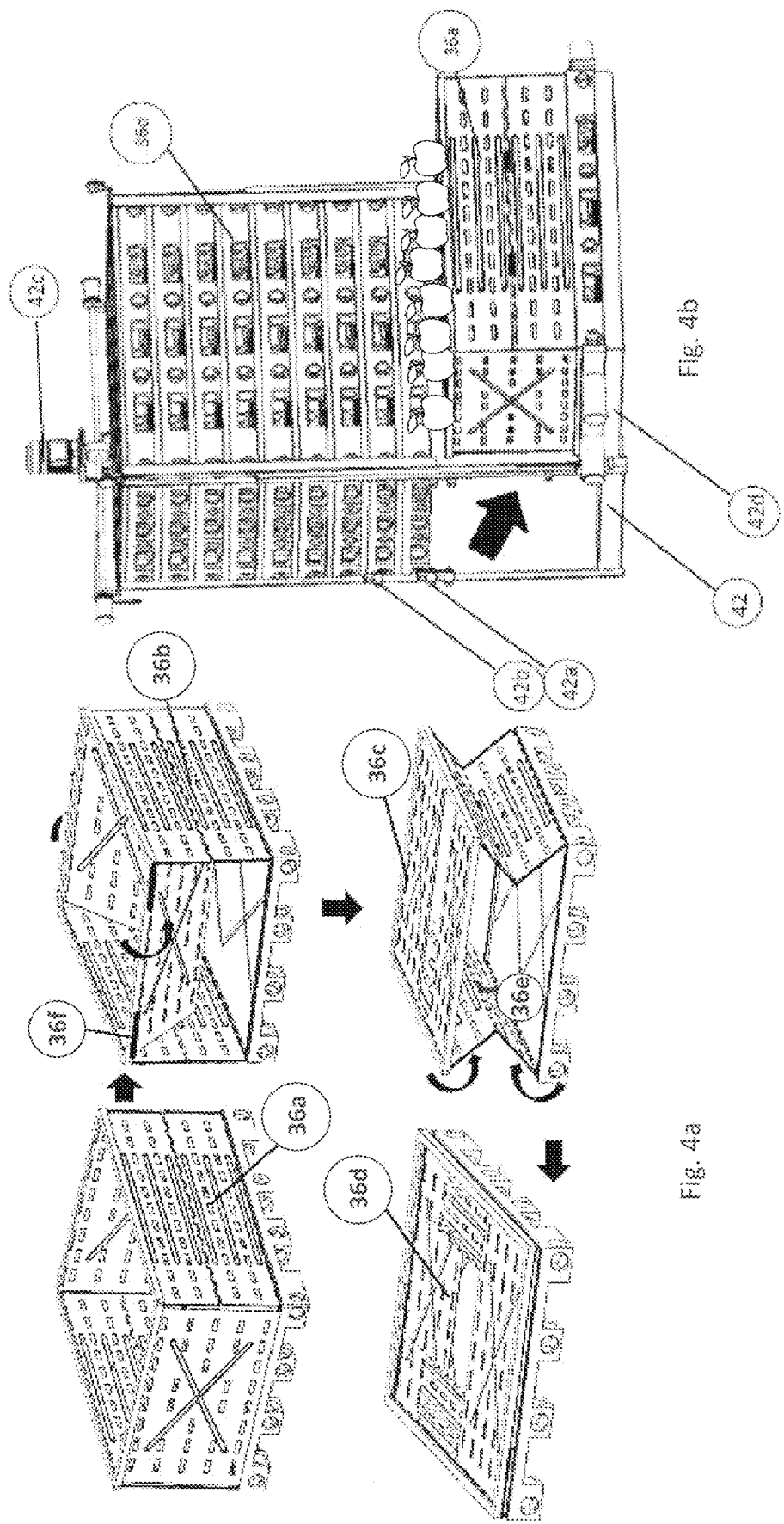

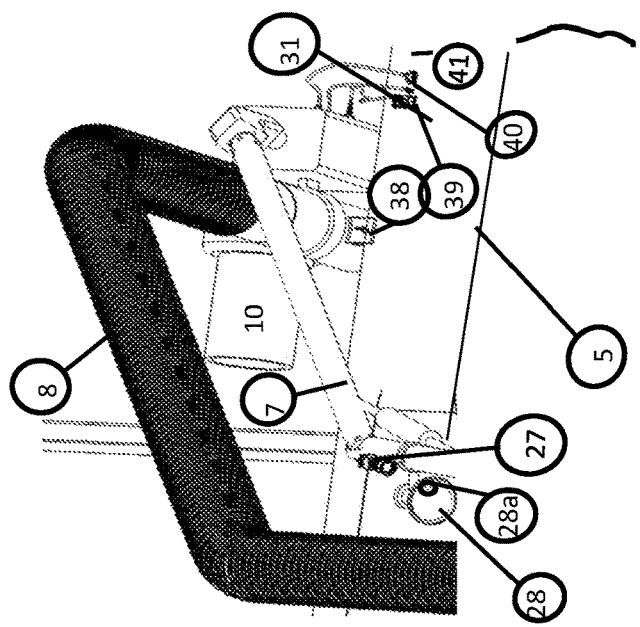
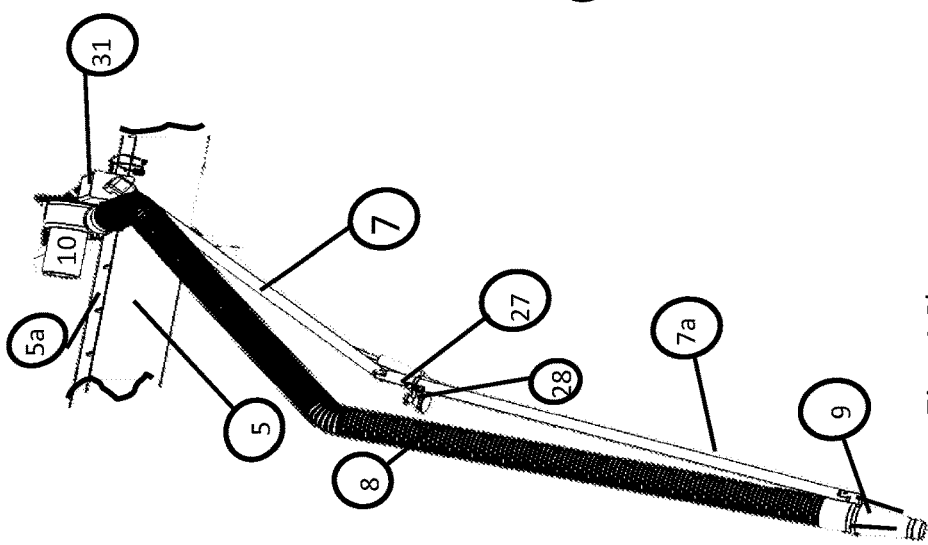
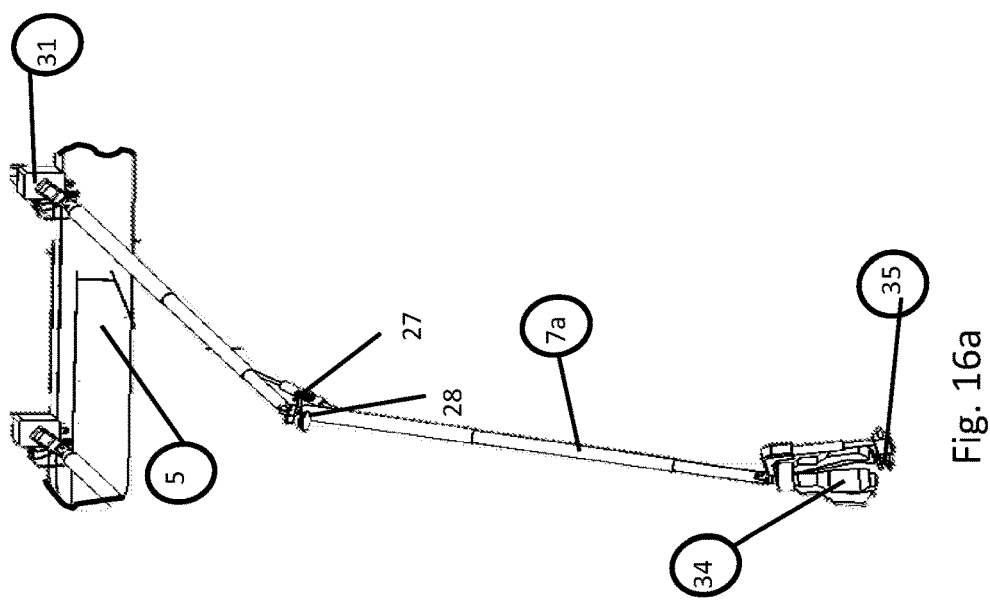

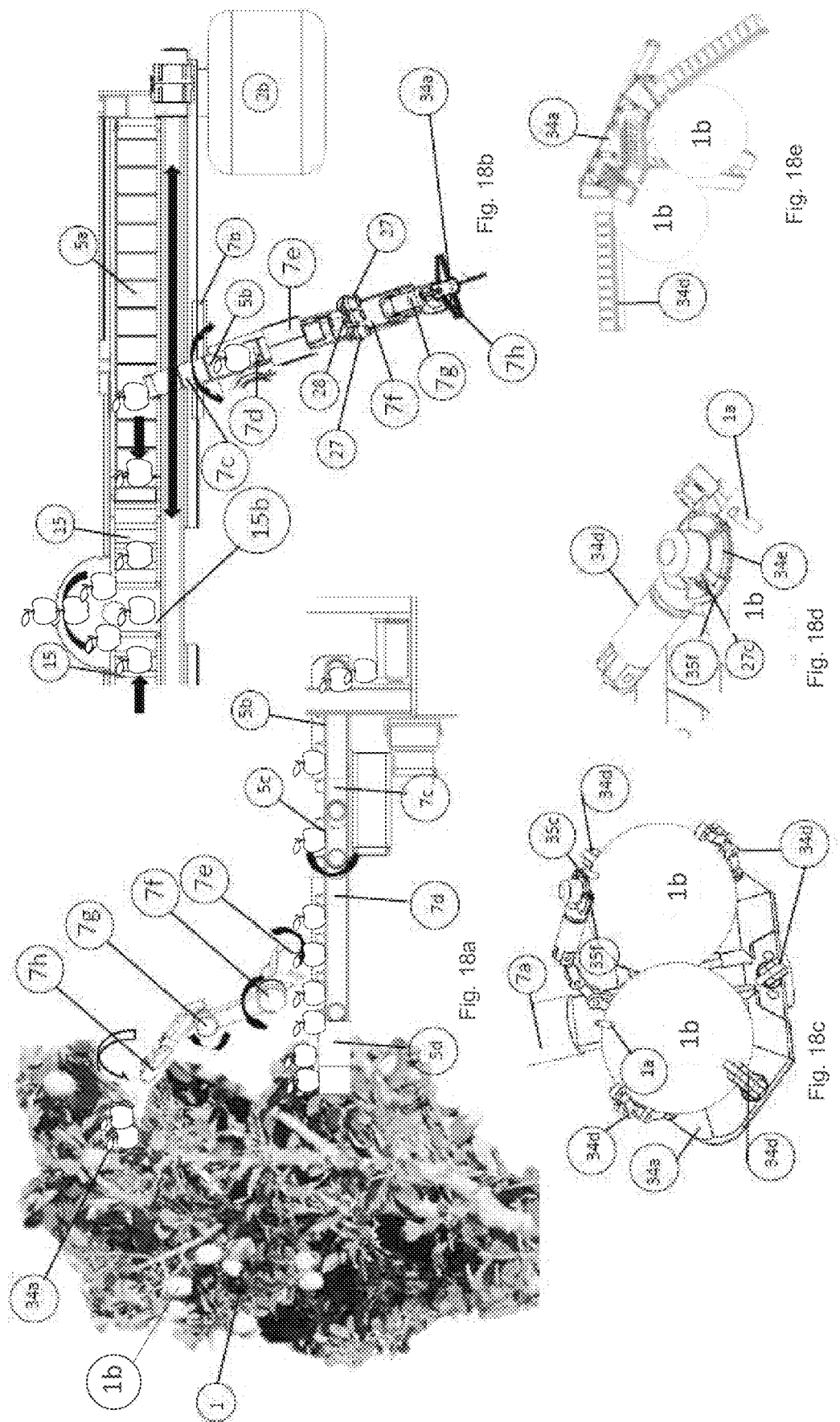

SELF-PROPELLED ROBOTIC HARVESTER FOR SELECTIVE PICKING OF HIGH QUALITY AGRICULTURE ROW CROPS

CROSS-REFERENCE TO RELATED APPLICATION(S)

This application is the U.S. national phase entry under 35 U.S.C. § 371 of International Application No. PCT/IL2018/050978, filed on Sep. 3, 2018, which claims benefit to Italian Patent Application No. 102017000099467, filed Sep. 5, 2017.

TERMINOLOGY

"SPFCH": Self-Propelled Field Crops Harvester for plurality of Agriculture products—a machine for smart selective harvesting.

"SPFCH-G": Self-Propelled Field Crops Harvester (-Ginning) specifically designed for cotton harvesting, ginning and cotton bale pressing.

"SPFCH-F": Self-Propelled Field Crops Harvester (-Fruits) specifically designed for orchard's fruit harvesting, and collecting them into bins.

Field row crops: Agricultural crops which grow in large scale open fields, on different width and kinds of beds, in a formation of rows, in which machines, tools and harvesters can propelled along them.

Crop: a vegetable or commodity (such as cotton) grown at outdoors fields

Seed-cotton: The material known as "cotton" which consists of both the seeds and its lint attached to the seeds.

Lint/fibers: The seed free fibers separated from the seeds which are used to manufacture yarns.

Cotton Seeds: the cotton seeds separated from its lint.

Ginning: A process aimed to separate the cotton lint from the seeds of the seed-cotton.

Contamination of cotton: foreign materials, such as plastic, polypropylene and alike which contaminates the cotton fields and eventually arrive to the ginning process grinded into many small pieces and by that contaminates the fibers.

FIELD OF THE INVENTION

The present invention relates to the field of crop harvesting, more particularly to automatic mechanic harvesters for harvesting various orchards fruits or open field crops including cotton.

BACKGROUND

In general, the current invention is aimed to harvest, e.g., field's crops or fruits, by robotics technics, at the crop fields or orchards, by the gentlest way possible, in order to preserve crops' quality. In the case of cotton, controlled ginning process can also be included.

The invention is related to smart harvesting of row crops and fruits, such as cotton, okra, artichoke, apples, stone fruits, citrus, etc., that are characterized by a gradual ripping process, during a relative long period of time. Crops, like cotton, artichoke and okra, are traditionally (and still) picked by human pickers, in some regions in the world, such as Africa, South America and China. However most of the table fruits grown in orchards are still harvested by human pickers.

For fruits that are grown for industrial purposes, such as for juice making, there are many kinds of commercial available harvesters that pick all the fruits on the tree at once, without selection, usually by shaking the fruits and/or the tree's main trunk and collecting the falling fruits with a collecting sheet or conveyor. This kind of harvesting picks not only fruits but also leaves, stems, etc. However, for selective high quality picking of fruits there are no harvesters.

The picking tasks are usually very backbreaking and tedious work and in some crops are also unpleasant due to little spines that exists in the crop (such as in okra, raspberries, artichoke, citrus, etc.). However, handpicking is still the best possible way to pick such crops while preserving best quality.

In case of okra, harvesting needs to be done every other day, from the beginning of harvesting, since it is harvested when the crop is at about 2 to 3 inches long. Harvesting it after this development age might disqualify it as an edible crop.

The same situation applies also to artichoke. The artichoke head needs to be harvested when it reaches a certain size according to each variety, and late harvesting might cause the artichoke to start opening its outer petals, which, in marketing terms, is becoming an inedible product. Therefore harvesting must be made at exact timing.

In case of apples and stone fruits, there is a need not only to pick mature fruits but also to thin the fruits' number prior to full maturation by selectively picking immature fruits, thereby enabling better quality fruit growth.

In orchards, the timing of the picking is of high importance, since late picking makes the harvested fruits too mature for commercial use.

US 2006/0213167 relates to harvesting of orchard's-based crops such as pome and stone fruits, using robotic-based picking of fruits based on scouting of the fruits in one robotic platform while the harvesting platform is installed on another platform. U.S. Pat. No. 4,519,193 reveals a robotic-based fruit picking arm with a picking and mechanical cutter, all within a vacuum tube.

For other crops, U.S. Pat. Nos. 5,768,869 and 4,191,008 disclose devices for cutting okra pods without touching the pod, but all must be done manually.

In case of hand-picked cotton, the opened cotton bolls are picked almost without any leaves or stems, in opposed to machine based harvesting, in which the seed-cotton is mixed with much of botanical and non-botanical materials such as crushed leaves, grass, stem's barks, hulls, bract, seed coats or stems, all may contaminate the final fiber product during processing. Therefore, seed-cotton after hand picking needs much less additional cleaning process prior to ginning. Traditional lint cleaner's process, within the ginning process, which is used to overcome the cleaning of the above mentioned contaminants, cause damage to the fibers and reduce the overall turnout of fiber during the ginning process.

In oppose to that, high throughput commercial cotton harvesters that exist today, such as the spindle type and the stripper type, harvest the clean cotton bolls together with its dry leaves stems and other botanical materials and by that contaminate the clean cotton and therefore dramatically reduce its quality.

Furthermore, as mentioned, cotton bolls do not mature at the same time, hence, the lower bolls are ripped first and the others, which are located higher and outer of the main stem, are opened gradually in the following weeks. However the higher and outer the boll from the main stem, the less its weight, fiber length, strength and maturity level. Mixing the heaviest, oldest, lowest and the very high quality bolls with the much younger and less mature bolls is bad to the textile chain, which buys the cotton as raw material, and looks for as much as uniform material as possible.

In the last 100 years, from the first invention of the spindle type cotton harvesters, the concept of commercial picking considering the best picking time when all yield is ready for picking. This concept has, as mentioned above, some disadvantages such as mixing mature and good quality cotton with immature and relative young bolls. This concept also puts the highest quality of bolls (the first to ripe) at risk to be rotten, e.g. due to high humidity, or to be contaminated by honeydew secreted by insects (a problematic material in the textile industry) which are active in the leaves above the open bolls.

Furthermore, in most of the cotton growing belts, worldwide, cotton fields are vulnerable to early rains or snow which reduce dramatically the cotton's quality by dust particles which are washed down from the atmosphere on the open bolls which was not yet harvested, due to the necessity to let the upper bolls be ripened and opened before harvesting. Another huge problem of late harvesting is accumulation of non-botanical contamination, such as plastic bags or transparent plastic that is often used on the ground in cold zones. These materials contaminate the lint during the ginning process, arrive to the spinning mills and increase the amount of defects in the fabrics made by the contaminated yarns, since the plastic do not absorb the die as the cotton fibers.

Prior art reveals that harvesting cotton by using vacuum is known from 1930 as the Cotton Pickers' Lament. http://www.britishpathe.com/video/the-cotton-pickers-lament (see also FIG. 19a and Ref. 4 below). It is based on propelled machine with electrical blowers connected to long air hoses which are directed to the individual boll for harvesting by a human picker. Exactly the same idea is detailed in U.S. Pat. No. 8,534,035. The idea of robotic cotton harvester is also disclosed in CN 201135036Y, in which a robotic arm is mounted on a self-propelled chassis, and aimed to pick limited amount of cotton and bring it to a cotton collecting hopper. Picking vegetable and fruit is also disclosed in CN 103503639B. Other mechanical small picking devices are commercially available. Some are based on motoric blowers connected to air hoses which are operated by human pickers as done about 80 years ago by Lament (https://youtu.be/yRmGWaIs41w) (FIG. 19b) https://www.youtube.com/watch?v=CAWZzF6CxA.

Manual and mechanical picking instruments, for manual hand picking cotton, based on pinching the fibers and transport them to a portable bag, are also commercially available and used in India and other countries, see e.g. FIG. 19c, https://www.youtube.com/watch?v=CAWZzF6CxA.

Cotton, in oppose to other crops, needs in addition to harvesting to undergo a ginning process in order to convert the picked seed-cotton into usable commodity. Ginning process separates the cotton seeds from the cotton lint. The fibers are used for yarn manufacturing while the seeds are used for extracting oil and/or for feeding cattle. The most common ginning processes are the saw-gin and the roller-gin. The first saw-gin machine introduced to the cotton industry and patented by Whitney in 1794, while roller-gin, invented by an unknown Indian inventor around the 16$^{th}$ century and its core technology remained virtually unchanged up to present time.

Traditionally, ginning process is done in dedicated factories. Seed-cotton (comprises also stems, trash, dust, etc.) is packed in the field by different technics (rollers, modules, bags, wagons, trailers, etc.) during harvesting, and transported by dedicated trucks to the gin yard for later ginning process during and after the cotton season ends. Common gin comprise of feeder, drying mechanism (since ginning requires the lint to be dry to a certain percent of moisture) pre-cleaning machines aimed to remove the big trash brought from the fields (such as green unopen bolls, stones, etc.) before ginning, and lint cleaning machines, aimed to clean the lint after the ginning process. These cleaning processes damage the fibers and reduce the overall lint turnout since certain amount of fibers are removed with the trash being removed.

As a common practice in different crops such as wheat, corn, rice, chickpeas and alike, separation of the seeds from the plant parts (stems and leaves) is made by a dedicated combine harvester which is designed to harvest the product, separate and accumulate the seeds in its own container and dispose all the rest back to the field. A different machine is then designed to collect the hay and compress it to compressed bales.

U.S. Pat. No. 9,475,189 describes a harvesting system that includes multiple robots, one or more sensors and one or more computers. The robots are mounted on a common frame facing an area to be harvested, and are each configured to harvest crop items by reaching and gripping the crop items from a fixed angle of approach. The sensors are configured to acquire images of the area, whereas the computers are configured to identify the crop items in the images, and to direct the robots to harvest the identified crop items. However, the system is limited in that the arms are parallel to each other and the fruits are reached from a fixed angle, thereby limiting the system to harvest only fruits that are not hidden behind tree's stems. Furthermore, each robot of the system is expected to pick a single fruit per about five seconds, while when touching an apple which is closed to another adjacent one within the same cluster, the other apple might fall down: Baeten et al. (ref. 5) states that "extra care should be taken in selecting the first apple in a cluster in order not to push off other apples". Therefore, both apples must be held and picked together in order to be picked properly. In U.S. Pat. No. 9,475,189 there is no explanation of the gripping mechanism other than stating that it is aimed for gripping one fruit. Publication of this invention (https://www.youtube.com/watch?v=UaL3UxUclKY) reveals a linear 3 finger gripper to grab one apple at a time.

U.S. Pat. No. 7,695,220 describes a vacuum hose aimed for transporting articles, such as apples, from a picking location on a tree to a collection bin or other site. The device includes a tube member adapted to receive and transport the articles, and a plurality of deformable baffles at spaced-apart locations within the tube. Each baffle defines an aperture which permits the article to engage and deform the baffle and aperture so as to move through the aperture and down the tube. The article is urged through the tube by a pneumatic pressure differential created across the article. This technology is good for round fruits like apples, but non-round fruits, such as pomegranates, will get stuck inside the tube due to their big crown and/or uneven shape. Therefore transporting of all kinds of fruits requires open but gentle transporter.

U.S. Pat. No. 7,882,686 describes a mobile system for improving hand-picking and preliminary processing of apples, citrus, stone fruit etc., the system comprises a mobile chassis upon which can be mounted picking stations, pneumatic tube transport subsystems, receiving and conveying subsystems, object scanning subsystems, cull diverter subsystems, labeling subsystems, and subsystems for relatively gently placing the objects in a predetermined location in a receiving bin. The system can also include a subsystem for gently placing diverted objects in a receiving bin.

Accordingly, a need exists for a fully automated harvesting machine/system. The present invention integrates modern optical and image analysis technologies and robotics with some of the old ones, such as traditional ginning and bale packing, to a powerful cotton combine that selectively harvest and gin the cotton at the same time and outputs cotton seeds which accumulates it in its own container and then removed to outside trucks, while in parallel compressing the lint, after ginning, into high quality cotton bales.

The invention further provides smart harvesting of different row crops.

SUMMARY

All the above mentioned disadvantages are avoided by changing the harvesting concept from one time harvesting of large amount of fruit/cotton at a short time, when all crop is ready to harvesting, to multiply rounds of selective harvesting of smaller amounts per plant, by robotic arms. For instance, in cotton, the harvesting will begin just short time after the lower bolls are ready to be harvest, and continued harvesting cycles will be performed until all ripe cotton bolls are picked. The same with apples. The red varieties, for example, will be picked when red by avoiding those which are still pink or green. Selective harvesting will avoid immature fibers or immature fruits to be picked. Plastic sheets, which are on the ground at a cotton field, will not be picked since the robotic arm(s) will be directed only to the bolls which are ready to be picked (like practice by hand picking of cotton). In case plastic sheets exist on the plant, the smart picking algorithm, assisted by data obtained from sensors, will instruct the harvesting arm(s) to skip the boll to avoid the contaminant to arrive to the ginning process. All the above mentioned must be conducted, automatically, while causing minimum damage to the plant, which is physiologically still active.

New robotics technologies enable future cotton and other row field crops harvesters to imitate hand picking while the plants are still green and active in terms of photosynthesis and accumulating carbohydrates to increase quality of its crop of the later fruiting bodies.

In the case of cotton, selective picking every mature boll, just after its opening, and a month before the upper bolls will be picked, has huge commercial value since this cotton will be sold in high prices. At the same time, keeping the plant active, without the need to defoliate the leaves, by chemicals applied to the fields, before traditional harvesting, also saves expenses, is better to the environment, and enables the upper bolls to mature better and increase quality, in oppose to the situation today in which the maturation of the bolls stops, due to defoliation of the leaves (hence no leaves remain to feed the young bolls to complete maturation).

The mentioned robotics technologies require optical detection means to distinguish if the crop that is ready to be harvested (such as open white cotton ball, okra size of 2-3 inch, artichoke at right size, apple in the right color according to its variety, etc.), within its green canopy and the brown leaves and stems.

Evaluation of the technologies disclosed for fruit picking reveals that robotic arms equipped with camera or stereo optics for scouting are public domain. These include the transporting means to a collecting bin. However, none of the known publications and solutions solves the unique situation of holding a fruit and cut it in a specific place without damaging the fruit.

The idea of using a robotic arm holding a fruit picking means, and navigating the arm to a fruit is mentioned in the prior art, e.g. in US 2006/0213167 and U.S. Pat. No. 4,519,193. However, a solution for the major problem of: (i) heavy-duty high reach of the picking arm, with a relative high payload needed at the fruit head point; (ii) a high picking rate; and (iii) picking and transporting, at the same robotic arm, of small fruits (such as apples, peach, plum or apricots) or big fruits (such as pomegranates or grapefruit), are not disclosed.

As to the cutting tools, the prior art discloses only the fact that a cutting tool is needed US 2006/0213167 (FIG. 3). However, a combination of smart sensing of the exact place of cutting (such as when cropping citrus or pomegranates) and a sophisticated way of sensing and cutting tool integrated within a grabbing hand, is not disclosed, but is part of the present invention.

Furthermore, US 2012/0096823 uses two kinds of cutting disks running at different directions to cut small stems, while at the current patent the cutting device is installed at the $6^{th}$ or $7^{th}$ smart finger that sense the surface of the fruit and direct the cutting finger to the exact location for best cutting and minimum damage to the fruit, according to each specific fruit.

As per the grabbing hand, the present invention offers a robotic hand, comprising 4-7 fingers, which is capable of grabbing a cluster of 2-3 fruits at a time. This feature is vital for efficient commercial fruit picking since it saves the time of reloading the picked fruits to the collecting catching device. The wrist and forehand of the present robotic hand(s) enables at least 2 additional degree of movement for maximum maneuverability for accessing fruits even if hidden behind a stem.

Logistics of providing bins for human pickers place important role during picking season. Bins need to be relatively close to the pickers and every few minutes bins are filled and need to be replaced with empty ones. Providing a large amount of common used bins is a problem due to their large size and the space they occupy. One of the commercial solutions is a trailer with 6-8 bins towed by a machine that assists human pickers in the logistics of the picking process. The present invention solves this logistic problem by integrating a magazine of multiple collapsible bins and an automatic system that detects when a bin is full and then activates an automatic system of lifting down the full bin to the ground and automatically load a new empty bin (FIGS. 4 and 5) while picking is continued.

Notably, having a bin on a robotic fruit harvester is disclosed in US 2006/0213167. However, carrying magazine of many collapsible bins, which enable efficient picking, and replacing them and automatically providing and opening a new empty bin, by automatic system, when the bin is full, is not disclosed.

Notably, while the prior art sometimes mentions vacuum and water systems for collecting, washing, drying and lifting harvested fruits into a bin, no prior art relates to the logistics of replacing the bins, during picking, once a bin is filled, and none relates to sorting the fruits by cull diverter subsystems when no bins are present to collect different fruits with different quality.

Special emphasis needs to be given to the fact that vacuum transporting, which is widely described, is limited to very specific fruit types (such as apples), but is not suitable for harvesting other types of fruits such as pears (due to their shape) or pomegranate (due to their size and crown). In such cases, open transporting belts equipped with rubber/silicon small fingers, is needed.

Various picking devices and cutting the fruit stem, when needed, are known in the art. For instance, U.S. Pat. No. 4,519,193 offers a central cutting device of fruit stem by using a set of 3 cutting blades operated at once within a sleeve of vacuum; U.S. Pat. No. 3,460,330 discloses a rotating blade; CN 201957458U offers a manual device for cutting stems and fruits at height without any sensing or protecting of the fruit; US 2012/0096823 describes a pruning and picking machine that is based on hydraulic forward-, middle- and rear-arms holding a picking device. However, this design does not have enough degree of freedom to enable high maneuverability of the arms, which prevents reaching fruits located, e.g., behind stems. US 2012/0096823 further describes a cutting device and a process of picking fruits without grabbing the fruit during the picking, but by only reaching the area of the fruit's stem, cutting the stem with a double teeth blades and let the fruit fall down to the ground or into a fruit catcher, and then into a vacuumed hose. This picking procedure is completely different from the presently claimed invention, which requires gentle grabbing of the fruit: The picking process of the present invention includes precise controlling of the position of the cutting, as well as placing the fruits carefully on a transporting belt in order to preserve their quality. In addition, contrary to known devices that cannot reach fruits behind stems and do not use a sensor to verify the exact cutting point, the harvesting arms of the presently claimed device have high maneuverability (FIGS. 18a-18e) that enables easy reaching to hidden fruits, and are designed to identify preferred cutting area to maintain fruits' quality.

In oppose to known vacuum oriented picking systems presented above, the present invention provides a "hybrid" robotic arm made of 2-3 degree of freedom of heavy duty transporting arms, which is also aimed to hold the high moments (FIG. 18a) while the next at least 2 additional degrees of freedom robotic parts enable the picking or thinning hand to maneuver between stems to the best position of picking 1, 2, or even 3 fruits in one cluster of fruits, by holding it with a finger type gripper, to be picked by maneuvering its wrist and or forehand in order to reach the cluster.

As per cotton harvesting, combining the smart and selective harvesting of the cotton bolls only with an immediate drying and ginning, during harvesting, will minimize the need of cleaning the seed-cotton before ginning and the lint after the ginning. It will also make the ginning process much simpler and cheaper, its turnout will be higher and the cotton quality will be much higher, due to less operation involve in handling the lint before baling. Smart harvesting will produce contamination-free cotton since the foreign maters, which arrive today to the ginning mill, will not be picked and processed.

Furthermore, quality control of cotton fibers is conducted today in special testing laboratories after sampling of the cotton during ginning. Ginning during harvesting will include sampling and even some online quality testing such as color, trash, length and Micronaire.

A combine/harvester according to the present invention, which separates cotton seeds from the lint and press the lint to bales, at the field level, does not exist or described.

In case of harvesting cotton, the SPFCH of the invention may also comprises at least one ginning unit and lint bale press that gin the seed-cotton during harvesting and accumulate the seeds in a self-container that needs to be emptied when full. Cotton bales or boxes full of other crop are accumulated on a tail lift platform or on a platform trailed after the SPFCH that are emptied or replaced when full.

The present invention is directed to high throughput, smart, robotic, autonomous or driver operated, harvester of row crops such as cotton, orchard's fruits such as apples pome and stone fruits, but also artichoke or okra, and alike, that are characterized by the need of selecting harvesting ripe crop, during relative long period of time, while the plant is still active. The invention comprises of a modular and autonomous self-propelled field crops harvester (SPFCH) device, for selective picking of crops.

The SPFCH of the invention is electrical, fossil fuel or any other energy powered self-propelled harvester. For clean energy, the device may be operated by high capacity rechargeable batteries, optionally recharged or partially operated by foldable and extendable solar panels.

Harvesting can be based on one SPFCH unit that is aimed for one task only (such as picking) or of two detachable units, one consist of just the self-propelled unit (FIG. 1b) consist of the propelled devices such as the wheels/rubber chains and its supporting devices such as the driver cabin, the engine & electricity generator, hydraulic and air pumps and its automatic driving means and the other is the functional unit (FIGS. 1a & 2) aimed for different agriculture tasks such as picking, thinning or pruning etc. Each can be totally different from the other in terms of mechanical, electrical and software needs but with common characteristics of the need of recognition, robotic arms, and unique algorithm for the needed task and its mechanical means to do that.

For example, an apple picking process requires picking means, very gentle transporting means of the apples from the tree to the bin, since apples are very sensitive to bruising, and relative complicated mechanisms of bin's changing. However, same operation of picking small apples, commonly named "mechanical thinning", does not requires all those means since the small thinned apples can be left on the ground. So in this case the module that is attached to the propelled unit comprises only simple grabbing unit with an algorithm that through the apples to the space between the trees (as exactly done by human thinners).

Same propelled unit can be attached to a totally different unit for picking cotton which needs also propelling, recognition, socking means, transporting means but also ginning and pressing of bales.

Accordingly, in certain embodiments, the present invention provides a SPFCH with a modular design that enables mix-and-match of the different harvesting means and other mechanisms according to the crop being harvested and the specific harvesting tasks. For instance, such modular design enables separation of the propelled mechanism and its supporting devices, hence the wheels, the main engine and generator, the hydraulic and compressing means to be detached from the modular picking and other task mechanisms, in order to enable easy converting from picking to thinning or pruning or from orchard to open field crops and vice versa, by just changing to different chassis modules.

Harvesting is done by one or more modular robotic harvesting arms hanged on modular booms mounted in the front, sides and/or rear side of the SPFCH. The plural harvesting arms comprising of crop picking mechanism such as vacuum or gripper and crop-identification optics, mounted on plural booms. The computing hardware and software system is dedicated to operate both the navigation of the harvester and the harvesting of different crops while avoiding picking undesired contaminants when exists.

The modularity of the SPFCH of the invention enables mounting the robotic arms on any predetermined hanging points, which comprise connectors for bidirectional communication, mechanical power supply and electricity.

For orchards, the picking/thinning device of the invention enables to pick not only one fruit but also more than one fruit (i.e. 2, 3 or more) at the same cluster (FIGS. 22a-22c) or some fruits adjacent to each other (FIG. 22d-e).

For fruits that require the cutting of their connecting stem, the picking hand according to the invention offers a cutting finger that operates after the fruit is grabbed by other fingers.

Transporting of the harvested crop from the plant to the container is done by a self-transporting system, mounted both on the arms, the booms and the main chassis, aimed to transport the crop regardless of its picking location surrounding the harvester.

In specific embodiments, e.g. when harvesting in orchards, the robotic arms may be mounted in 2 or more levels in order to reach both high and low fruits on the same tree.

Thus, the present invention provides a modular, driven or autonomous self-propelled field crops harvester (SPFCH) device, for selective picking of crops, the device comprising: (a) an electrical, fossil fuel or any other energy powered self-propelled harvester; (b) one or more modular, robotic harvesting arms, each harvesting arm comprising a crop picking mechanism and crop-identification optics, gentle transporting means, fruit catcher, and also finger type cutting device, wherein each harvesting arm is adapted for vertical, horizontal and/or back and forth movements for accessing crop as well as for delivering harvested crop to, e.g., conveyor belts (on the arm or boom); (c) a computing system comprising a processor and a memory adapted for detecting crop to be harvested and potential contaminants, and for operating the robotic harvesting arms; (d) one or more modular booms, each modular boom comprising secured hanging points to mount the at least one or more modular robotic arms in accordance to the crop being harvested, each secured hanging point comprises electricity connectors, identification (ID) based data connections, and optionally air/oil pressure connectors, wherein the connectors transmit signals, electricity and/or mechanical power between each harvesting arm and the computing system. The signals may be transmitted by any suitable communication mean, such as Bluetooth or local WiFi, for the recognition, movement and harvesting orders; (e) a main container or bin for collecting harvested crop; (f) a first conveying system, mounted-on each robotic arm for collecting and transporting harvested crop and then transporting it to a common transporting unit serves all harvesting units and/or booms into the main container or bin; (g) optionally, a packing unit for packing the harvested crop; (h) optionally, a flat hydraulic tail lift platform for collecting harvested crop and/or packed harvested crop (e.g. cotton bales or boxes full of harvested crop); (i) a second conveying system, or lift, for emptying harvested crop from the SPFCH main container when full (FIG. 15), by belt or spiral kind of transporter when field crops are harvested, or by an automatic replacer of (collapsible) bins when orchard's crops are harvested, in which the bins are held on the SPFCH in a magazine(s) of collapsed folded bins located thereon. In addition, the SPFCH may comprise a separate lift that reloads the full bins to the ground while a new folded/collapsed bin is automatically opened while the picking process is continued (FIGS. 5a-5c).

In certain embodiments, the present invention provides a modular, human driven or autonomous/automatic self-propelled field crops harvester (SPFCH) device, for selective picking of crops, the device comprises: (a) a detachable propelled carrier system of an automatic or self-propelled harvester consisting of a propelled driving device and associated supporting mechanisms; (b) a modular chassis, designed to be attached to the detachable propelled carrier system, the modular chassis comprises one or more modular, robotic hybrid harvesting arms, each arm comprises of: a proximal-end, a distal-end, and at least one robotic joint enabling either vertical and/or horizontal movement, wherein: the proximal-end comprises a crop transporting mechanism designed to transport the harvested crop/fruit toward the SPFCH; and the distal-end (shorter) comprises a picking head comprising: crop-identification optics; at least one sensor for sensing at least one of: proximity, rigidity, torque force for picking and grabbing, size, color, shape, and brightness of the crop/fruit to be harvested; and a crop picking mechanism, the distal-end is designed to identify and harvest the fruit/crop and deliver same to the crop transporting mechanism of the proximal-end, wherein: the distal-end enables at least 2 more degrees of maneuverability for better accessibility of the picking head to the fruits/crop within the tree environment; the crop picking mechanism is selected from a detachable finger-like, a gripper and a suction, or any combination thereof, and each one of the robotic hybrid harvesting arms is adapted for vertical, horizontal and/or back and forth movements for accessing the fruits/crop and deliver same to a fruit/crop collecting catcher for further transporting toward the SPFCH; (c) a computing system comprising a processor and a memory adapted for: receiving data from the crop-identification optics; detecting crop to be harvested and potential contaminants; and operating all the robotic harvesting arms; (d) one or more modular horizontal or vertical boom, each modular boom comprising secured hanging points to mount the at least one or more modular robotic arms selected according to the crop being harvested, each secured hanging point comprises electricity connectors, identification based data connections, and optionally air/oil pressure connectors; (e) a container/bin/box for collecting the harvested crop; (f) a first conveying system for transporting harvested crop from each harvesting arm and/or boom into the container/bin/box; (g) optionally, an automatic container/bin replacer when container/bin is full; (h) optionally, a flat hydraulic tail lift platform for collecting harvested crop and/or packed harvested crop; (i) optionally, a magazine holding collapsible/foldable bins/boxes and an automatic bin/box replacer mechanism designed to automatically open/unfold the collapsible/foldable bins/boxes whenever a bin/box is filled and needs to be replaced; (j) a second automatic conveying/lifting system for emptying harvested crop from the SPFCH container in case of field crops, or downloading a bin to the ground, when full, in case of orchard's crops, in order to enable continues picking; wherein the computing system controls: the SPFCH navigation; the movement speed during harvesting, according to signals obtained by each one of the robotic picking arms; each one of the harvesting arms according to data obtained from the crop-identification optics, the type of crop being harvested, and/or the selected harvesting- or other task algorithm; and each one of the crop picking mechanism, according to signals obtained from the sensors and/or optics.

Notably, the computing system controls all operations of the SPFCH and its different components, e.g., SPFCH navigation and synchronizes movement speed during harvesting, according to signals obtained by each of the robotic picking arms, and each of the harvesting arms according to data obtained from the crop-identification optics, the type of crop being harvested, and/or the selected harvesting algorithm.

In certain embodiments, the SPFCH device of the invention further comprises at least one of: (a) a packing unit for packing the harvested crop; (b) a cassette holding folded bins/boxes; an unfolding mechanism for unfolding the folded bins/boxes; and a transporting mechanism for replacing a full bin/box with a new empty unfolded bin/box; and (c) a crane to pile bins/boxes of crop or crop-bales on top of each other and to efficiently order them on a collecting platform.

In certain embodiments, the SPFCH device of the invention further comprises at least one of: (1) a manual or automatic crane to pile boxes of crop or bales on top of each other and to efficiently order them on a collecting platform; (2) a set of rechargeable batteries that operates all electric systems thereof; and (3) solar panels for recharging the rechargeable batteries and/or for operating the SPFCH when day light is available. Otherwise the fusil fuel motored electric generator is activated, automatically, and provides the needed electricity; and a central electric circuit that manages the electricity generated by the solar panels and synchronizes same with the main electrical system of the SPFCH and its motored generator. In specific embodiments, the solar panel is foldable and/or extendable in order to increase light receiving area. In specific embodiments, the solar panels are foldable and/or extendable solar panels for recharging a rechargeable power source and/or for directly operating the SPFCH when day light is available and for protecting against dazzle at an acute angle, and a central electric circuit that manages the electricity generated by the solar panels and synchronizes them with the main electrical system of the SPFCH and its motored generator.

In certain embodiments, the SPFCH device of the invention further comprises a navigation system comprising GPS and/or guiding sensors, for controlling/navigating the SPFCH on roads and/or within a field to be harvested and while harvesting.

In certain embodiments of the SPFCH device of the invention, each of the at least one modular booms further comprises transporting belt/conveyer for transporting harvested crop from each harvesting arm to a main container or bins, optionally via a main conveyer.

In certain embodiments of the SPFCH device of the invention, each one of the modular horizontal or vertical booms further comprises: (i) pre-designed safety hanger points with connectors for electricity, communication and air/oil pressure which works independently regardless the boom's mounting position; and (ii) transporting belt/conveyer for transporting harvested crop from each harvesting arm to the main container, optionally via a main conveyor. In certain embodiments of the SPFCH device of the invention, the harvesting arms are mounted on the boom at a pre-designed safety hanger-points at an order suitable for the specific crop to be harvested. In yet other embodiments, each harvesting arm functions independently from one another, regardless of its mounting position.

In certain embodiments of the SPFCH device of the invention, the crop-identification optics comprise any one of: CCD colored/black & white camera, photodiodes, laser, illumination (e.g. IR, UV, visible, optical filters, laser, etc.), or any combination thereof, according to the harvested crop and method of its identification.

In certain embodiments, the SPFCH device of the invention, comprises any combination of the following one sensors such as:

In yet other embodiments, the computer uses data obtained from the crop-identification optics to automatically recognizes the ready for picking one or more fruits/crop within a fruit's cluster by using an algorithm according to the type of fruit/crop being harvested; instructs the harvesting arms to pick the one or more fruits/crop within the fruit's cluster, and transport the harvested fruit/crop to the conveyer system that transfers the crop to the container/bin/box.

In specific embodiments of the SPFCH device of the invention, the crop-identification optics further comprise a laser/radar (commercial available) rangefinder to check the range toward the crop to be harvested.

In certain embodiments of the SPFCH device of the invention, the harvesting arms further comprise a local vacuum generator and hose; or gripper optionally with a cutting tool, e.g. mounted as a special and additional cutting finger, which enables to cut the stem of a crop while grabbing the fruit by the other fingers, without the need of a second tool for cutting; or any combination thereof.

In certain embodiments of the SPFCH device of the invention, the conveying system comprises boom's conveyers, mounted on the booms, for transporting harvested crop from the harvesting arms to a main conveyer that transports the harvested crop to a central container or bin.

In specific embodiments of the SPFCH device of the invention, the crop is cotton, and the robotic harvesting arms of the SPFCH device of the invention comprise vacuum harvesting arms, and the SPFCH further comprises: (i) one or more vacuum generating unit; (ii) one or more ginning units, i.e. roller-gin units or saw-gin units for separating cotton lint from the seeds; (iii) temperature controlled heated conveyors for delivering harvested seed-cotton from the booms to the ginning units while drying the seed-cotton before ginning; (iv) a bale press for pressing the seed-free cotton lint into bales, and a conveyer for transporting ready bales to a collecting trailer platform or to a tail hydraulic lift platform mounted at the rear side of the SPFCH; (v) cotton seeds' container and (vi) mechanism for emptying the container from cotton seeds and/or the bale's platform to enable continues harvesting. In specific embodiments, the vacuum generating unit is: (i) a local vacuum generating unit designed to create independent vacuum in each harvesting arm; or (ii) a central vacuum generating unit mounted on the main chassis, and the booms are rigid, and optionally foldable, hollow tubes for transporting seed-cotton from the picking arms to the gins and/or container/s.

In certain embodiments, when the crop is cotton, the SPFCH device of the invention further comprises at least one of: (a) a sampling device of every bale for quality and a control unit for determining the quality of cotton lint fibers, and optionally for conducting online quality testing such as color, trash, length and Micronaire; (b) a controlled heating unit for heating the heated conveyers, optionally together with a (motored or electric) dedicated generator or other power source; (c) a gin stands feeder hopper, optionally comprises a spiral conveyor, designed to feed the gin stands in a controlled capacity, and a controlled heated conditions, e.g., by controlled hot air or any other drying unit, that feeds seed-cotton to the ginning feeder hopper; and (d) a conveyor, optionally spiral, that lifts and transports the cotton seeds from the bottom of the seeds' container into a separate wagon or truck.

In certain embodiments of the SPFCH device of the invention, when the crop is cotton, the heated conveyors are temperature controlled hot air streams within tubes. In specific embodiments, the tubes comprise inside a plurality of partitions mounted as labyrinth aimed to increase the tube/duct length and to enable longer exposure of the cotton to the heating and drying process.

In specific embodiments of the SPFCH device of the invention, the robotic harvesting arms are crop-gripper/hand-type arms that further comprise automatic cutting mechanism (e.g. movable knife, rotating cutting disk, open/close scissors, burning laser, etc.) to cut the fruit's holding stem while grabbing the fruit without the need of an additional tool for cutting. The arms are designed to gently grip the crop, after positive recognition thereof, and cut its connecting stem, and subsequently to transfer the harvested crop to the conveyor belt mounted on the arm or boom. In yet other specific embodiments, the crop-gripper is a hand-like picking tool having 4-7 fingers, wherein at least one of the fingers optionally constitutes the cutting tool.

In specific embodiments of the SPFCH device of the invention, when the crop is light (e.g. cotton), the picking mechanism of the SPFCH is vacuum and each harvesting robotic arm further comprises a hose connected to a local or main vacuum generator. In specific embodiments, the crop picking mechanism further comprises a gripper, aimed for heavy crops such as artichoke, and optionally also a cutting tool to cut the stem of the crop.

In specific embodiments of the SPFCH device of the invention, the crop is not cotton, and each robotic harvesting arm comprises: (i) a crop-gripper mechanism (e.g. movable knife, rotating cutting disk, open/close scissors, burning laser, etc.) designed to gently grip the crop and transfer the harvested crop to a conveyor belts mounted on the arm and the boom; and (ii) an automatic cutting mechanism designed to cut the crop's connecting stem. The arms are designed to gently grip the crop, after positive recognition thereof, and cut its connecting stem, and subsequently to transfer the harvested crop to the conveyor belt mounted on the arm or boom. In yet other specific embodiments, the crop-gripper mechanism is a hand-like picking tool having 4-7 fingers, wherein at least one of the fingers optionally constitutes the automatic cutting tool.

In specific embodiments of the SPFCH device of the invention, the fruits' gripper is a human-hand mimic, having 3 or more fingers-like elements, e.g. 3-5, 3-6, 3-7, 3-8, 4-5, 4-6, 4-7, 5-6, 5-7, or more, e.g., 5, 6 or 7 fingers-like elements. In specific embodiments, one of the fingers is a special "cutting finger" designed to act as a cutting element/finger and equipped with, e.g., a cutting disk, mounted on the tip of the finger. After determining the outer surface of the fruit and the exact cutting position, the cutting-finger is activated and harvests the fruit.

In specific embodiments of the SPFCH device of the invention, the crop is cotton, and the SPFCH further comprises: (i) one or more vacuum generating units connected to a vacuum hose located on each one of the harvesting arms; (ii) one or more ginning units, for separating cotton lint from the seeds; (iii) temperature controlled heated conveyors, ducts or tubes, for delivering and feeding the harvested seed-cotton from the booms to a ginning feeder hopper of the ginning units while drying the seed-cotton before ginning; (iv) a bale press for pressing the seed-free cotton lint into bales, and a conveyer for transporting ready bales to a collecting trailer platform or to a tail hydraulic lift platform mounted at the rear side of the SPFCH; and (v) a cotton seeds' container. In specific embodiments of the SPFCH device, the heated conveyors, ducts or tubes comprise partitions mounted as labyrinth, aimed to increase the length of the conveyor/tube/duct. In yet other specific embodiments, the SPFCH device further comprises: (i) a controlled heating unit for heating the heated conveyers, ducts or tubes, optionally together with a dedicated generator or other power source; (ii) a spiral or conveying mechanism for emptying the cotton seeds' container and/or the bale's platform to enable continues harvesting; and/or (iii) a sampling device designed to obtain a sample from every bale for assessing quality of the lint/fibers.

The present invention further provides a process of harvesting row crops comprising the steps of: (a) attaching the propelled unit to the functional unit according to the agriculture task required (b) transporting a SPFCH device of the invention to a field for multiple harvesting or other tasks iterations, within a crop season, and during its seasonal period (i.e. by driving on its own wheels/chains, while its booms or robotic hands are folded/dismantled and its solar panels are folded), and mounting/assembling the booms (with the harvesting arms) in the field before harvesting; (c) selective harvesting automatically by: recognizing automatically ready-for-harvest crop and possible various contamination using crop-identification optics, and picking desired (ripe) crop only, while avoiding picking possible contaminants; (d) transferring the harvested crop to a transporting system/conveyer, mounted on the booms or the robotic hands, that transports the harvested crop to a main transporting system, that transports the harvested crop to a collecting container/bins while sorting them, optically, by a limited and basic major quality parameters, and/or packing unit; and (e) emptying or transferring the collecting container/bin and/or packed crop into an accompanying wagon or truck or by unloading them from the SPFCH to the ground.

The present invention further provides a process of selective harvesting row crops comprising the steps of: (a) attaching a detachable propelled carrier system to a modular chassis as defined above, by connecting the mechanics, hydraulic, pneumatic, to obtain the SPFCH device of the invention; (b) if not in the field, propelling the SPFCH to the field/orchard; (c) activating the SPFCH device thereby enabling it to harvest automatically either by slow continues movement or in cycles of stationary picking intervals and then moving the SPFCH to next stationary picking station while: (1) recognizing ready-for-harvest crop as well as various contaminations (e.g. in case of cotton); (2) picking desired crop only, while avoiding picking the contaminants (e.g. in case of cotton); (3) optionally, when diluting/thinning orchard's fruits before picking, using modular units suitable for recognizing and picking small fruits and discarding same, while avoiding the need for accumulation them but direct them to the space between trees; (4) transferring the harvested crop by a gentle transporting system/conveyer; (5) optionally, sorting the fruits by cull diverter subsystems; and (6) emptying or transferring the collecting container/bin/box and/or the packed crop to an accompanying wagon or truck (in case of open field crops), or to the ground (in case of orchards crops).

In certain embodiments, the process of the invention further comprises at least one of the following steps: (i) prior to step (a), assembling onto the booms harvesting robotic arms according to the crop to be harvested in terms of type of arms or picking heads, amount and mounting order thereon; (ii) adjusting the amount and position of the harvesting robotic arms on each boom(s) according to the field and crop to be harvested, in terms of number and density of rows, and crops' density and plants' size; (iii) manually or fully automatically guiding the harvester by sensors and/or GPS; and (iv) sampling every container/bin/box or crop's (e.g. cotton) bale for assessing quality control.

In specific embodiments of the process of the invention, for orchard's use, the harvester operates at a station-mode, contrary to a continues-mode, so that the harvester stops moving during the picking, and continue moving forward to the next picking station only when the picking is complete at the present picking station, and so on.

In specific embodiments of the process of the invention, the harvesting is fully automatic and guided by sensors and GPS.

In other specific embodiments of the process of the invention, the crop is cotton, and the robotic harvesting arms are vacuum harvesting arms, and the SPFCH further comprises: (i) one or more vacuum generating units connected to a vacuum hose located on each one of the harvesting arms; (ii) one or more ginning units, i.e. roller-gin unit or saw-gin units, or any other ginning mechanism, for separating cotton lint from the seeds; (iii) temperature controlled heated conveyors, ducts or tubes, for delivering and feeding the harvested seed-cotton from the booms to a ginning feeder hopper of the ginning units while controlling the drying of the seed-cotton before ginning; (iv) a bale press for pressing the seed-free cotton lint in bales, and a mechanism/conveyor for transporting ready bales to a collecting trailer platform or to a flat tail hydraulic lift platform mounted at the rear side of the SPFCH; and (v) cotton seeds' container, wherein the process further comprises the following steps: harvesting the cotton by vacuum only or by a combination of pinching and vacuum, while avoiding picking possible contamination when exists, and transporting same to a ginning unit while temperature controlled heating and drying the harvested seed-cotton; ginning the seed-cotton to separate cotton lint fibers from cotton seeds; controlling the ginning speed and capacity for best cost performance; transporting the cotton lint to a bale press and creating cotton bales; transporting the cotton bales to a trailed platform or a flat hydraulic tail lift; accumulating the separated cotton seeds in a seeds' container; and unloading both the seeds from the container and the bales from the platform out of the SPCFH to enable continuance harvesting, i.e. when both are full and block the harvesting.

In certain embodiments, the process of the invention further comprises a step of gripping each bale by a manual or automatic crane that piles the bales on top of each other and efficiently order them on a collecting platform.

In specific embodiments, the process of the invention further comprises steps of grabbing at least two lint samples from each bale for quality control. In such embodiments of the process, the step of transporting the cotton bales to a trailed platform or a flat hydraulic tail lift, may be accompanied with a step of transporting one of the samples together with the bale for quality testing, while storing the other lint sample on the SPCFH for backup and/or for further quality testing, optionally conducted on and by the SPCFH.

In specific embodiments of the harvesting process of the invention, the crop is not cotton, and each (hybrid) robotic harvesting arm of the SPFCH further comprises: (i) a crop-gripper mechanism designed to gently grip the crop and transfer the harvested crop, gently, to a conveyor belt mounted on the boom; and (ii) an automatic cutting mechanism designed to cut the crop's connecting stem, wherein the process further comprises the step of harvesting the crop by gripping only the crop to be harvested with the crop-gripper mechanism and cutting the stem (when needed) with the automatic cutting mechanism. In specific embodiments of the process of the invention, the SPFCH further comprises a cassette of folded bins/boxes and a mechanism for unfolding them, wherein the process further comprises the steps of transporting a full bin/box to the ground.

In specific embodiments of the process of the invention, the automatic selective harvesting step further comprises a step of returning each harvesting arm to its zero position, after finishing harvesting, prior to the movement of the SPCFH to the next harvesting point.

In specific embodiments of the process of the invention, the navigation of the SPCFH in the field is manual or fully automatic and guided by sensors and GPS.

BRIEF DESCRIPTION OF THE FIGURES

FIG. 2b demonstrates the process of lifting down the bin (36a) to the ground when the bin is full.

FIGS. 3a-3c are schematic views of a SPFCH's module for picking tree's fruits showing the components for automatic feeding of collapsible bins when needed to replace a full bin of fruits. FIG. 3a is a front view; FIG. 3b is a top view showing two stations of bins and a magazine of collapsible bins, as well as the flow of the fruits from the tree to the bin via transporting belts located both on the robotic arms and inside the SPFCH and the sorting toward bin one or bin two; FIG. 3c is a bottom view showing the mechanism of automatic replacement of the bins.

FIG. 4a is a schematic isometric view of 4 positions of a bin from fully open state into a fully fold bin.

FIG. 4b shows an isometric view of the automatic bin exchanger showing the magazine of many fold bins aside one bin at fully open state during picking.

FIG. 5A shows the lift mechanism to drop of full bins to the ground; FIG. 5b shows the unfolding of the fold bin by activating and releasing lockers; FIG. 5c shows the movement of an open bin from the magazine to the lift position.

FIGS. 16a-16c illustrate several possible modular robotic arms according to the invention: FIG. 16a is a detailed drawing of a modular robotic arm and its crop-identification optics for mounting on any of the booms for possible use of gripping and cutting the stem of crops like artichoke and alike. FIG. 16b is a detailed drawing of a modular robotic arm and its crop-identification optics for mounting on any of the booms for possible use of vacuum to harvest crops like cotton and alike. FIG. 16c is a detailed drawing of a modular connection of a robotic arm to the boom, further detailing the local vacuum source of the arm, the vacuum hose, the electrical connector and its cable, air/oil connectors and communication cable accordingly.

FIG. 18a-18e are zoom views of a robotic arm and its gripper/hand-like picking tool, including the option for a cutting device mounted on each robotic arm. FIG. 18a emphases the unique design of the 7 degrees of freedoms (DOF) of which 3 comprise a gentle transporter and 4 enable high maneuverability within the tree's canopy; FIG. 18b is a top view emphasizing the 3 DOF that comprise a transporting means that operates in as a part of the movement of the arm toward a cluster of fruits; FIG. 18c is a top view of a human-like robotic hand; FIG. 18d is a top view of a human-like robotic hand showing the close and dust-free position designed to protect the mechanism from the dusty and humid canopy environment while also protecting the fruits from the disk blade/cutting means. FIG. 18e is a top view of the soft fingers of a robotic hand, showing the option of grabbing fingers made of soft materials such as silicon with inside solid materials as functioning as "bones" and activated by air or hydraulic forces.

FIG. 19a—old Lament vacuum harvesting; FIG. 19b—vacuumed based cotton picking by motored vacuum and manual devices; FIG. 19c—manual cotton picking device based on pinching; and FIG. 19d—common practice of harvesting artichoke.

FIG. 19a vs. FIG. 19b for artichoke; FIG. 20c vs. FIG. 20d for okra; and FIG. 20e vs. FIG. 20f for cotton.

FIG. 22a shows apples in horizontal position before picking; FIG. 22b shows how a human picker grabs 2 apples in a horizontal position; and FIG. 22c shows how a human picker turns 2 apples into a vertical position. FIG. 22d shows human picker picks the 2 apples in a horizontal position; and FIG. 22e shows the tree after the picking.

FIG. 23a-reaching the $1^{st}$ apple; FIG. 23b-picking the $1^{st}$ apple; FIG. 23c-reaching and picking the $2^{nd}$ apple while holding the $1^{st}$ apple.

FIG. 23d shows the 2 apples before grabbing; FIG. 23e shows the 2 apples grabbed by an artificial robotic hand; FIG. 23f shows the $1^{st}$ apple released from the artificial robotic hand; FIG. 23g shows $2^{nd}$ apple released from the artificial robotic hand; and FIG. 23h shows the artificial robotic hand grabbing a big fruit such as pomegranate.

FIG. 26a demonstrates mounting robotics arms for cotton harvesting at low density plants. FIG. 26b demonstrates mounting robotics arms for cotton harvesting at high density plants.

FIG. 27a when solar panels are in full extending position and when sun might dazzle the cameras and it is necessary to protect against the dazzle at an acute angle (especially at sunrise and sunset) in order to produce good images; and FIG. 27b when harvesting below a net, e.g. in orchards that are covered by upper shedding nets (44a) held by pillar poles (44), while solar panels are in its folded configuration.

DETAILED DESCRIPTION

Figure 1A:
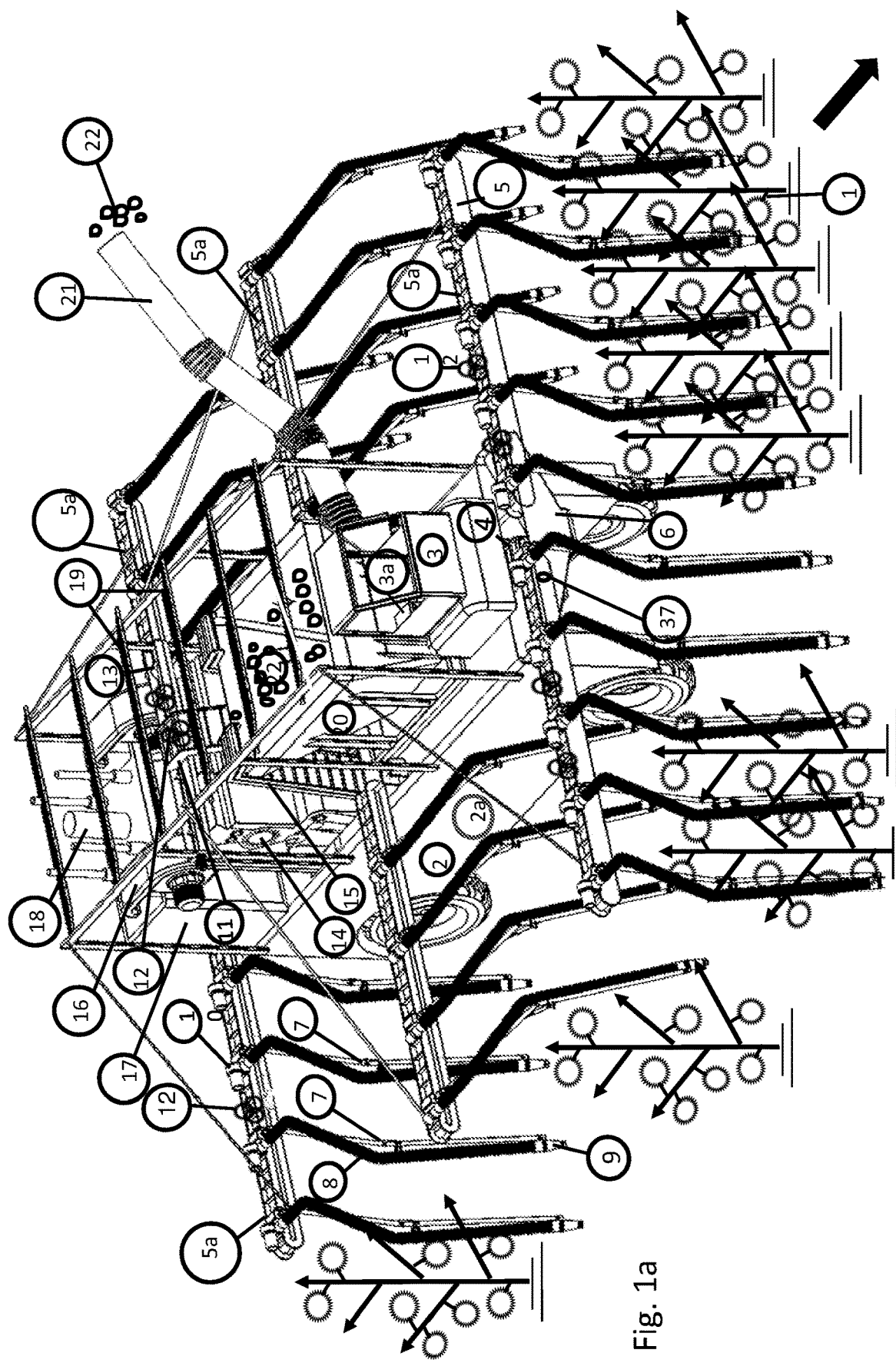
FIG. 1a is a schematic isometric view of the cotton and ginning module SPFCH-G of the invention, within a row cotton field, detailing the position of the booms, the different transporting mechanism, elevators and containers, power unit including, the solar panels, ginning and the pressing mechanism, the seed's container, and the ability to hang plurality of picking robotic arms either in the front rear and side of the SPFCH.
Figure 1B:
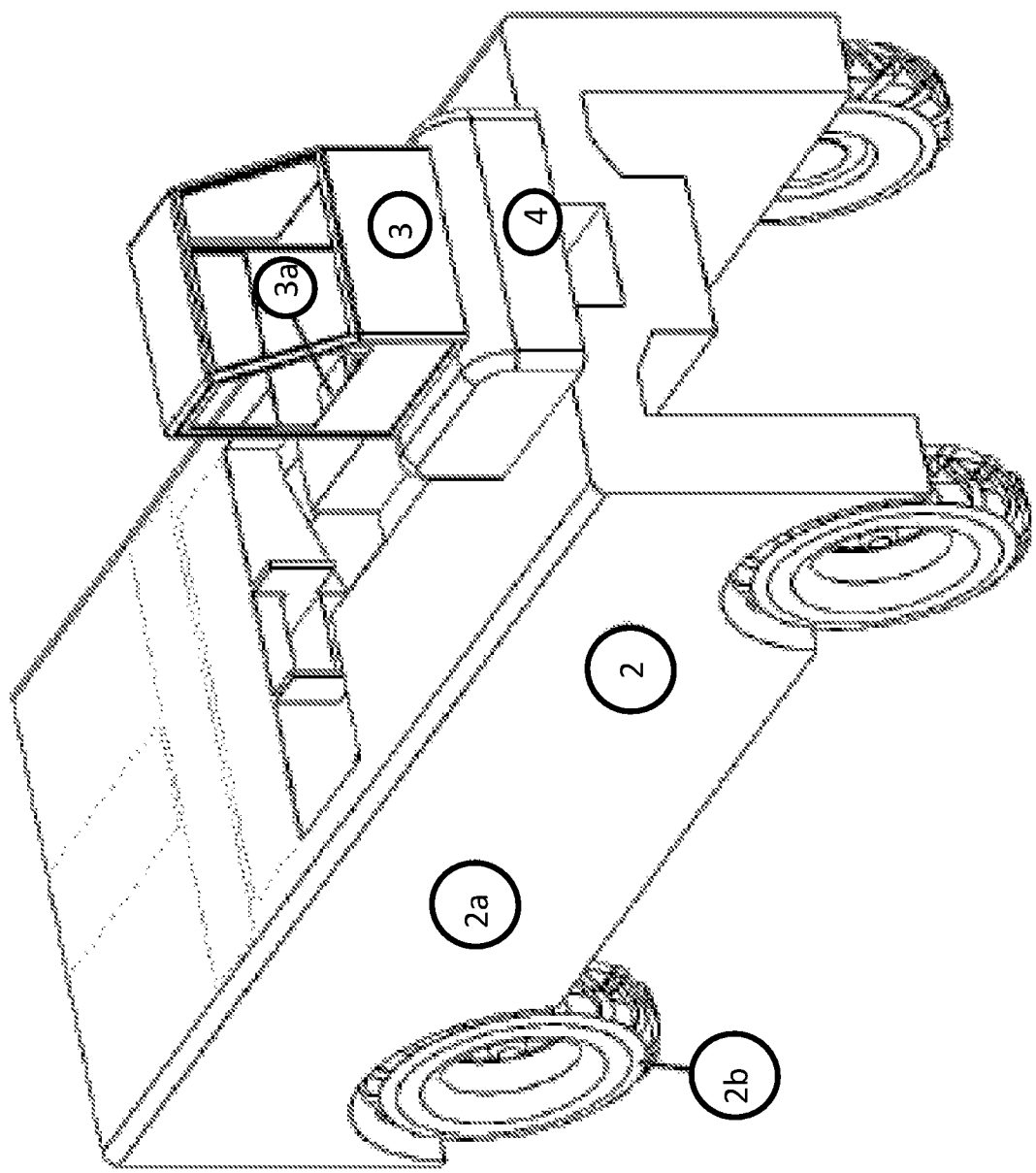
FIG. 1b is a schematic isometric view of the propelled system carrier only without any functional unit attached to it.

The present invention provides a Self-Propelled Field Crops Harvester, "SPFCH", system mounted on high chassis (1b), for selective picking of high quality field row crops, by plurality of modular robotic arms mounted on modular booms, which may be mounted in front, rear or sides of the SPFCH in one levels or more, while each of the plural robotic arms equipped with its optical device such as CCD camera or line camera and illumination devices of any wave length chosen such as visible, IR, UV, laser or else, for automatically recognizing the ready and ripen crop, by special algorithm for each different harvested crop, hidden or above the green or other color of leaves, and other botanical material, within the crop's canopy, and picking them, individually or in clusters, by vacuum hose or grippers, attached to the outer part of the robotic arm, operated and moved toward the crop, by motors embedded inside the arm's joints which are instructed to move by communication sent from the SPFCH central computer. The recognized crop is then vacuumed or cut and then transferred by the vacuum, or by the robotic arm, to a transporting belt, located on the boom, mounted on the SPFCH, which transfer the crop toward a main conveying belt, also located on the SPFCH, which collects all the harvested crops from all the transporting belts, surrounding the SPFCH, and lift them all into a collecting container, or harvesting boxes, which when full is able to empty itself out of the SPFCH into an assisting wagon or truck.

In certain embodiments, the system of the invention compromises: (a) a main high and self-propelled wheel/rubber chain drive harvester, powered by motored or electric generator, aimed mainly, but not limited to, for charging a set of chargeable batteries, mounted within the chassis of the harvester, which operates all systems, the SPFCH is driven on roads by human operator or during harvesting by automatic system, which navigates itself by rows guiding sensors, assisted by GPS, the movement of the SPFCH is controlled by a programmable controller and or by its central computer, which synchronize the speed of the movement, during harvesting, according to signals obtained by each of the robotic picking arms, at the end of each individual picking cycle of process; (b) a single or several modular booms on which transporting belts or rigid hoses are mounted, with a possibility to operate in both directions, the booms can be mounted in front, side, or rear sides or all of the sides, the booms comprise at least one secured hanger to mount a modular robotic arm and its optics, the booms also comprise pre-designed hanging points aimed to mount the robotic arms in a certain combination suitable to the crop harvested and its exact growing agro-technic, each point comprises of connectors of electricity, wired or wireless ID based data connections and air/oil pressure connectors, which are connected prior to harvesting, the connectors transmit the signals by communication devices such as Bluetooth or local WiFi, installed on the SPFCH, for the recognition and movement orders communicates between the robotic arms and its algorithm on the SPFCH, all aimed to connect the robotic arms and its optics, via the booms, to the computer; (c) a plurality of individual crop's harvesting robotic arm units comprising at least one robotic motored joint to enable vertical movement, one robotic motored joint to enable horizontal movement, so that the arm will be able to access a single or cluster of crop in one position, or to bring the crop to the conveyor belts mounted on the boom in the other position. If needed, the robotic unit can be mounted on the boom at a pre-designed safety hanging points, aimed for fast replacement, at an order suitable for the specific crop, to enable any kind of the SPFCH robotic unit to function, regardless of its mounting position, the outer part of the robotic arm (the one close to the plants) might comprise an enlargement mechanism to enable the arm to access a fruit hidden inside the canopy, the outer side of each robotic arm or near to its joint, comprising also tiny CCD colored camera or photodiodes, illumination of any kind such as IR, UV, visible, laser or else as best suitable for detecting the harvested crop, possibly also a laser or radar rangefinder mounted aside the optical device to check the range toward the crop to be harvested, a transparent cover to protect the optics, cutting tool to cut the stem of the crop, in case needed, a local vacuum hose or gripper, attached to the outer and last part of the robotic arm, enable sucking of lightweight crops to the transporting belt located on the boom; (d) a main conveying system for collecting harvested crop from all booms into the main conveying system which lifts the crop into a main container located on the SPFCH; and (e) a system to empty the harvested crop from the SPFCH, when full, to a wagon or truck or to download it to the ground.

In certain embodiments of the system of the invention, the SPFCH comprises, in addition to the motored generator for recharging the batteries, also foldable and extendable solar panels that save fusil fuel when sun is available.

In specific embodiments, the system further comprises: (a) at least one solar panel adequate to the size of the upper part of the SPFCH, as big as possible, and might also be foldable for driving on roads and unfold and extendable to its maximum collecting area in order to increase electric power during harvesting; and (b) a central electric circuit that manage the electricity generated by the foldable solar panels and synchronized with the main electrical system of the SPFCH, which stops the fusil fuel motored generator when foldable and extendable solar panels provides all the electrical needs for the SPFCH operation and restart it when needed.

In certain embodiments, the SPFCH system of the invention is aimed for non-cotton crops, such as artichoke, wherein the SPFCH further comprises, in addition to the robotic arms and transporting mechanism, grippers and automatic cutting mechanism such as vibrated or moveable knife, rotating cutting disk, open/close scissors, burning laser or else, aimed to gently grip the crop, after positive recognition, and then to cut its connecting stem, and then to transfer the crop, by the robotic arm, to the conveyor belt, mounted on the boom or on the transporting part of the robotic arm, toward the central convening belt mounted on the Self-Propelled chassis, which direct the crop to the accumulation container or collecting boxes.

In specific embodiments, the system further comprises: (a) a robotic arm on which the gripping module is mounted; (b) a modular gripping mechanism of any new or commercial design, comprising at least two fingers, at a size suitable for the crop harvested, such as big gripper for artichoke or small gripper for okra; (c) a movable cutting mechanism of at least one cutter, at a size suitable for the crop harvested such as relative large moving knife or rotated disk for artichoke and small for okra or apples, so the cutting tool is designed to be adjacent to the gripping device; and (d) a communication devices between the main computers, exist on the SPFCH, and the gripper and cutting module to activate the gripping and cutting in the right order (first recognition, then gripping, then cutting and then move toward the transporting belt located on the boom).

In certain embodiments of the system of the invention, the Self-Propelled Field Crops Harvester-Gin for cotton ("SPFCH-G"), further comprises, in addition to the robotic arms and transporting mechanism, single or several stands of roller or saw-gin units and one bale press, and heated conveyors for drying the seed-cotton, before ginning, and accumulate the seeds after ginning in the main container and compress the lint into bales while grabbing samples for quality control of the fibers, and possibly conducting online quality testing such as color, trash length and Micronaire, all mounted on the self-propelled chassis.

Flat hydraulic tail lift mounted on the rear side of the SPFCH-G might be an option to replace the trailed platform.

In certain embodiments of the system of the invention, the booms holding the robotic units, do not comprise transporting belts and the local vacuum blowers, for sucking the seed-cotton, but the vacuum is produced by a central strong blower/s located on the SPFCH, and the picked lightweight crops are sucked by long hoses held in one side by the robotic arm and in the other side connected to a main rigid, but foldable, duct, mounted on the booms, connected to the main strong blower inlet.

In specific embodiments, the system comprising: (a) long rigid and flexible vacuum hoses mounted between the robotic unit and the main vacuum blower; (b) at least one main blower; and (c) an air duct connected to the outlet of the blower aimed to flow the crop from the robotic arm directly to the container/basket or to the gin's heating lift hopper.

In yet other specific embodiments, the air duct connected to the outlet of the main seed-cotton blower, aimed to collect the seed-cotton and to direct it to the gin's feeding hopper, is heated by controlled hot air or other mechanism, in order to dry the seed-cotton to certain desire moisture content before ginning.

Accordingly, in certain embodiments, the system of the invention comprises: (a) a duct connected to the seed-cotton blower in one side and to the gin's feeding hopper in the other side; (b) a plurality of controlled heaters or hot air heaters that dry the seed-cotton inside the duck while flowing; and (c) possibly, a plurality of inside partitions mounted as labyrinth aimed to increase the duct length and to expose the seed-cotton more time to the heating and drying process. Heating mechanism are controlled by temperature sensors which regulate the hot air temperature in order to avoid overheating and burning.

The present invention further provides a process of harvesting row crops by a Self-Propelled Field Crops Harvester, "SPFCH". After determining the type of crop that is to be harvested/treated or the harvesting task therefor, the specific module(s) is attached to the universal carrier. Then, when the system arrives to the potential field for harvesting by driving on its tire wheels/rubber chains, while its booms and solar panels are folded, or separated booms carried by its trailer to be mounted in the field, then selective harvesting is done automatically by unfolding the solar panels and then activate plurality of modular robotic arms mounted on modular booms, which may be mounted in front, rear or side of the SPFCH, while each of the plural robotic arms equipped with its optical device, such as CCD camera or line camera or photodiodes and illumination devices of any wave length chosen such as laser, visible, IR, UV or else, for automatically recognizing the ready and ripen crop, by special algorithm for each different harvested crop, hidden or above the green or other color of leaves, and other botanical material, within the crop's canopy, and picking them, individually or in clusters, by vacuum hose or grippers, attached to the outer part of the robotic arm (the one close to the crop), operated and moved toward the crop, by motors embedded inside the arm's joints which are instructed to move by communication sent from the SPFCH central computer, the recognized crop is then vacuumed or cut and then transferred by the vacuum, or by the robotic arm, to a transporting belt, located on the boom, mounted on the SPFCH, which transfer the crop toward a main conveying belt, also located on the SPFCH, which collects all the harvested crops from all the transporting belts, mounted surrounding the SPFCH, and lift them all into a collecting container, or harvesting boxes, which when full is able to empty itself out of the SPFCH into an assisting wagon or truck or downloaded to the ground according to the crop harvested;

In certain embodiments, the process of the invention comprising: (a) a main self-propelled wheel/rubber chain drive harvester, build as a one unit or as a detachable two units, powered by motored or electric generator, aimed to be able to bring the SPFCH, driven by a driver, to the field and during harvesting; (b) a powerful electrical system, powered by fusil fuel engine or by chargeable batteries, charged by either the public electrical system, foldable and extendable solar panels or fusil fuel generator, aimed to provide both electricity and air/oil pressure to activate the different processes of the SPFCH; (c) prior to the harvesting season the operator must set the SPFCH robotic arm's positioning and picking module (vacuum or grippers) according to the harvested crop and the density of the rows; (d) once the positioning and density of the crop is set and the harvester arrived to the field, the automatic computerized picking system is activated by the driver; (e) selective harvesting is done by the plurality of modular robotic arms mounted on modular booms, which may be mounted in front, rear or side of the SPFCH, while each of the plural robotic arms equipped with its optical device such as CCD camera or line camera or photodiodes supported by optical filters, and illumination devices of any wave length chosen such as laser, visible, IR, UV or else, for automatically recognizing the ready and ripen crop, by special algorithm for each different harvested crop, hidden or above the green or other color of leaves, and other botanical material, within the crop's canopy, and picking them, individually or in clusters, by its gripper, attached to the outer part of the robotic arm, (the one near the crop) operated and moved toward the crop, by motors embedded inside the arm's joints which are instructed to move by communication sent from the SPFCH central computer, the recognized crop is then gripped, its connecting stem is cut; (f) cutting is electronically synchronized to cut the stem, connecting the crop to its plant, by a signal sent by the main algorithm, after the crop is gripped by the gripper; (g) once the crop is cut then it is transferred by the robotic arm to the closest transporting belt, mounted on the boom, which is mounted on the SPFCH and transferred toward the accumulation container or directly toward dedicated boxes; and (h) harvesting process is fully automatic guided in the rows by sensors and assisted by GPS.

In certain embodiments of the process of robotic picking of field crops of the invention, a Self-Propelled Field Crops Harvester-Gin, for cotton, "SPFCH-G", a specific harvester for quality cotton picking, as detailed above, is used. The system arrives to the potential field for harvesting by driving on its tire wheels/rubber chains, while its booms and solar panels are folded, or separated booms carried by its trailer to mounted in the field, selective harvesting is done by plurality of modular robotic arms mounted on modular booms, which may be mounted in front, rear or side of the SPFCH-G, while each of the plural robotic arms equipped with its optical device such as CCD camera or line camera and illumination devices of any wave length chosen such as laser, visible, IR, UV or else, for automatically recognizing the ready and ripen crop, by special algorithm for each different harvested crop, hidden or above the green or other color of leaves, and other botanical material, within the cotton canopy, and picking them, individually or in clusters, by vacuum hose, attached to the outer part of the robotic arm, operated and moved toward the crop, by motors embedded inside the arm's joints which are instructed to move by communication sent from the SPFCH-G central computer, the recognized crop is then vacuumed and then transferred by the vacuum, to a transporting belt, or rigid hose mounter on the boom, which mounted on the SPFCH-G, then the picked seed-cotton is transferred toward a main heated conveying belt, also located on the SPFCH-G, toward the feeding hopper of the gin stand while drying the seed-cotton, after the gin process is completed, the separated seeds are directed to the accumulation container and the lint is directed by vacuumed to the bale press to be baled and removed out of the harvester onto a trailed platform.

In certain embodiments, the process of the invention comprises: (a) a main self-propelled wheel/rubber chain drive harvester, aimed to be able to bring the SPFCH-G, driven by a driver, to the field and during harvesting; (b) a powerful electrical system, powered by chargeable batteries, charged by either the public electrical system, foldable and extendable solar panels or fusil fuel generator, aimed to provide both electricity and air/oil pressure to activate the different processes of the SPFCH-G; (c) prior to the harvesting season the operator must set the SPFCH-G robotic arm's positioning and picking module (local vacuum or central vacuum) according to the harvested crop and the density of the rows; (d) once the positioning and density of the cotton growing is set and the harvester arrived to the field, the automatic computerized picking system is activated; (e) in parallel, the ginning stands, heaters in ducts and ginning rate need to be set before starting harvesting; (f) pressing the Start picking button, by the driver, activates the robotic arms to start searching for ripen crop; (g) followed by the computer order, any arm is automatically, and autonomic suck the seed-cotton and commute the main system when finished, before getting back to its waiting zero position, the last arm to finish, confirms movement of the SPCFH-G to its next position, dictated by the algorithm, specifically for each picking stage; (h) all the autonomic robotic arms, no matter its positioning surrounding the SPFCH, transfers the crop to the main transporting system that feeds the gin hopper; (i) ginning process starts simultaneously when the ginning hopper is full; (j) cotton seeds separated after the ginning process are falling down by gravitation under the ginning stand and then lifted into the accumulation container by belt or spiral conveyor; (k) once the container is full another spiral conveyor is activated toward a receiving to a wagon or truck; (l) in parallel, the lint, separated from the seed-cotton, transfers by vacuum duct toward a lint slide, which direct them toward a pressing duct, in which a press piston pressing the lint and then is pulled back, to be able to receive the next portion of lint, until the bale size is finished, and then a manual of automatic tightening device install bands to fix the bale final dimensions; and (m) navigation within the harvesting process is fully automatic guided by sensors and assisted by GPS.

Figure 20E:
FIGS. 20a-20f are examples of original pictures of agricultural products, as seen by a CCD camera and their digital segmentation for harvesting as done by computerized algorithm. Presentation of three typical original pictures vs. their digital segmented image of different crops (artichoke, okra and cotton) is demonstrated.
Figure 20F:
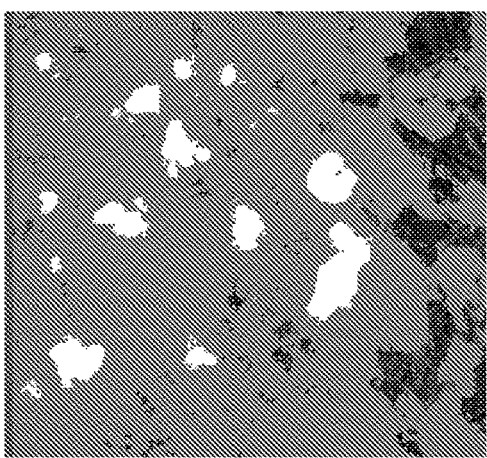
Figure 20C:
Figure 20D:
Figure 20A:
Figure 20B:
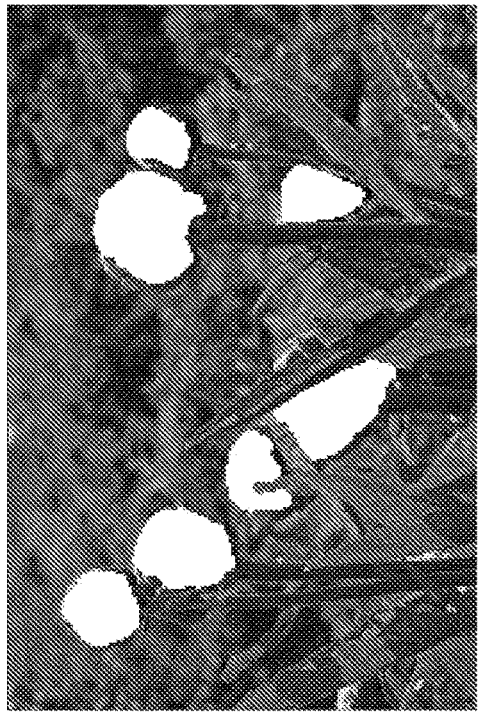
Figure 21B:
FIGS. 21a-21b are examples of original apple tree pictures, as seen by a CCD camera and its digital segmentation for harvesting as done by computerized machine learning algorithm.
Figure 21A:
Figure 22F:
FIG. 22f shows how a robotic hand according to the invention grabs 2 apples similar to a human picker.
Figure 22C:
FIGS. 22a-22e demonstrate the picking action of 2 apples at once by a human.
Figure 22B:
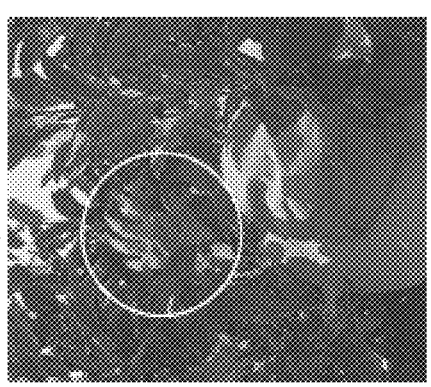
Figure 22E:
Figure 22A:
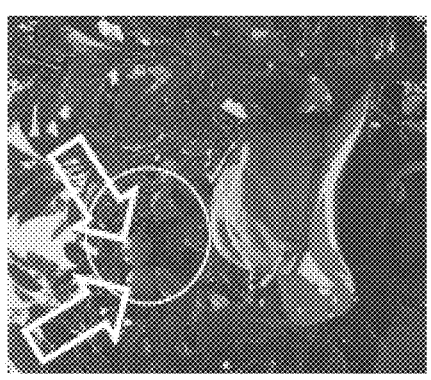
Figure 22D:
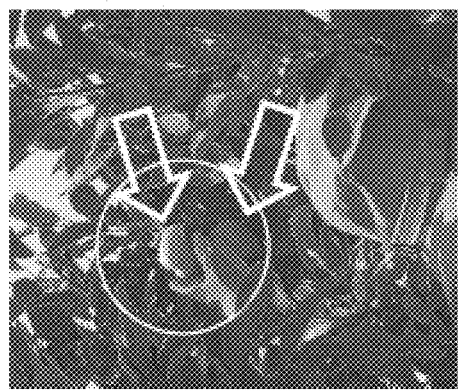
Figure 23A:
FIGS. 23a-23c demonstrate picking of 2 apples in two consecutive steps by a human picker.
Figure 23B:
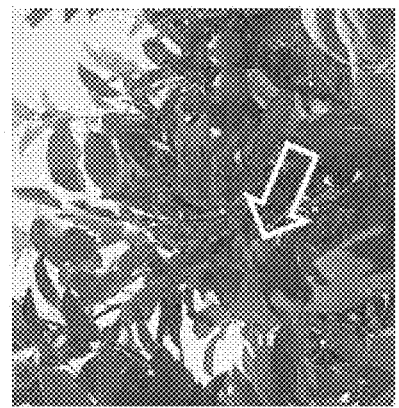
Figure 23C:
Figure 23H:
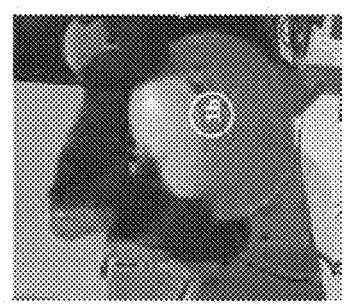
FIGS. 23d-23h demonstrate grabbing of 2 apples at ones by an artificial robotic hand.
Figure 23G:
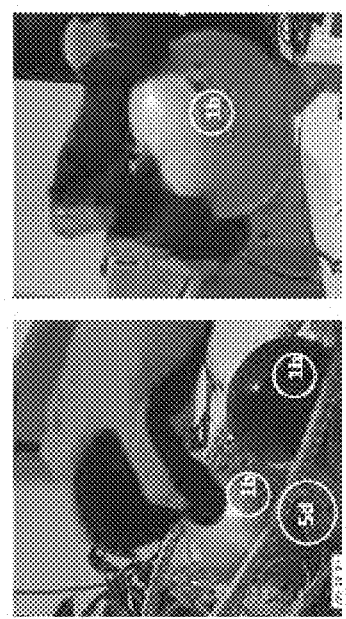
Figure 23F:
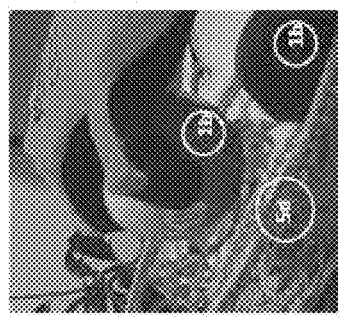
Figure 23E:
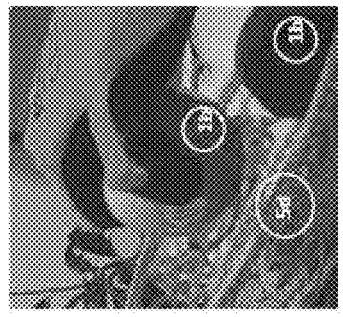
Figure 23D:
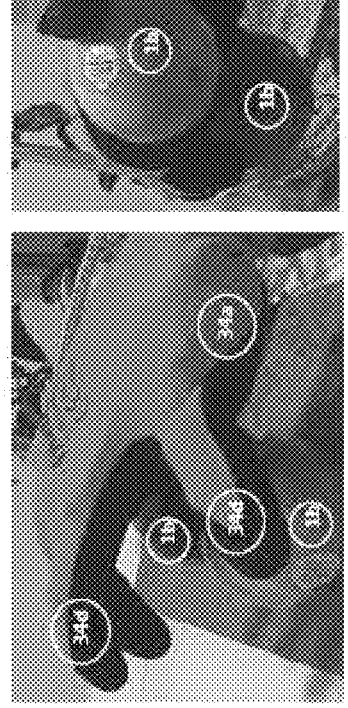

The recognition of crop (fruits and vegetables) within a view of green leaves and brown leaves (old leaves) is covered by many academic papers published at the last 25 years (see e.g. Refs. 1 & 2 below), demonstrating that recognition of fruits within fruit trees or white cotton within its natural environment of green leaves, brown/yellow stems and brown ground, is possible (FIGS. 20 & 21).

In case of tree's fruits, such as pome and stone fruits, the fruits are scattered all over the tree canopy, many of them hidden behind leaves or stems, which forces the algorithms being used to recognize the fruits while overcoming these obstacles. In case of artichoke, the heads to be harvested are on the top of the plant and are easy to be detected and cut. Okra needs more challenging and gentle detection & picking tools but its detection is also feasible as shown in FIG. 20d.

Accordingly, the present invention provides a unique algorithm for distinguishing between crops that need to be harvested and the plant canopy, as well as various contaminants. In addition, the algorithm is designed to distinguish between crop that is ready for the pick, and those that are not. As demonstrated in FIGS. 20b, 20d, 20f and 21b, the algorithm of the invention is used to identify artichoke, okra, cotton and apples, respectively, while distinguishing between green canopy and fruit or open boll (in case of cotton) as well as between mature and immature fruits or fully opened and ready to be harvested and not fully opened and ready that will be picked at the next harvesting round. For instance, in the case of okra, the fruit's size is the leading criteria for harvesting.

The algorithm to be used is determined according to the type of crop being harvested. Therefore, the digital recognition of the crop to be harvested is tailor made by machine learning or deep learning algorithms, for each crop as needed.

In certain embodiments, a SPFCH central computer system comprises more than one algorithm for all crops of which it is designed to harvest. Thus, the SPFCH of the invention is flexible and can switch between harvesting one crop and another by merely replacing the mechanical module(s), the software/algorithm and the robotic picking arms/tools, e.g., from vacuum (in the case of cotton) to grippers (for artichoke, etc.) or to hand-like grippers in case of orchards' fruits. In addition, the SPFCH of the invention can further switch from field module with booms (for artichoke or cotton) to orchards' mode (with two levels of robotic arms) by mere changing the equipped chassis as needed.

After recognition of the fruit/boll/crop to be harvested, a gentle picking mechanism is also needed.

Figure 19C:
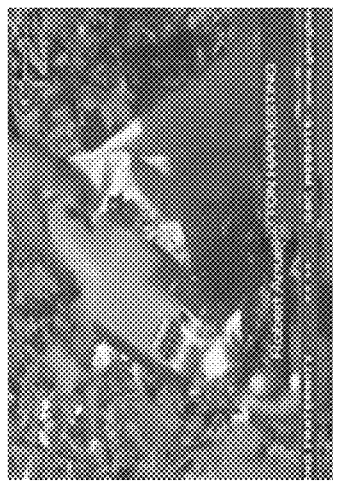
FIGS. 19a-19d demonstrate different vacuum-based harvesting of cotton.
Figure 19D:
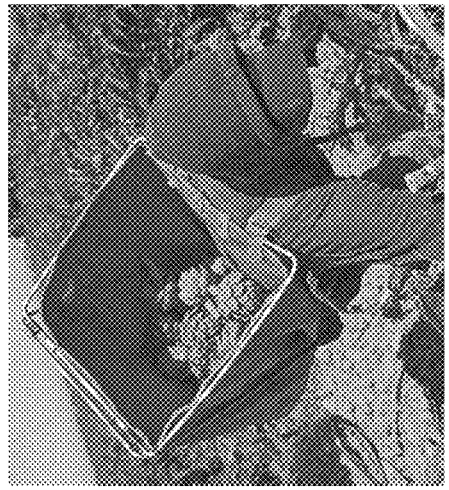
Figure 19A:
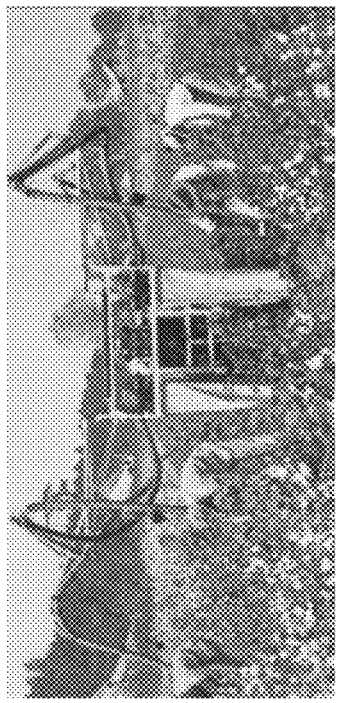
Figure 19B:

In case of cotton, a vacuum (FIG. 19b) or other mechanical pinching technics (such as that illustrated in FIG. 19c) are required to pick a single- or some close bolls at a time, without or with minimal picking of leaves or stems, and with minimum scratching the stems, which might bring stem's barks to the fiber's mass.

In case of orchards' fruits, a more sophisticated robotic human hand-like arm (e.g. as illustrated in FIGS. 18c & 18d) is required, to enable strong, but gentle, grabbing of one or more fruit and in order to enable detaching it from its stem.

In certain embodiments, when there is a need to detach a fruit by cutting its stem (e.g. for citrus and pomegranates) the robotic harvesting arm of the SPFCH of the invention further comprises an additional cutting-element/finger 35c, dedicate for cutting the stem. In an exemplary embodiment, such a cutting finger is equipped with a tiny high speed cutting disk, run by air turbine or micro-motor. In specific embodiments, the integrated tiny cutting tool 35c is directed by a camera and/or a touch sensor that senses the surface of the fruit toward the exact cutting position. The cutting tool is pressed against the fruit stem 1a of the fruit (1b) by the robotic cutting finger while overcoming the elasticity power of its silicon/rubber cap 35d, or activating the opening of the blade protector, aimed to protect the fruit from the cutting disk 35c. Such a combination of a robotic palm-hand equipped with a cutting tool, enables picking and cutting fruits by using a single robotic arm, contrary to human picker or other known devices that require two-hands picking: one for grabbing the fruit and the other for operating the cutting means.

In the case of crops which require cutting, such as okra, artichoke or alike, a mechanical gripper will hold the crop and an automatic cutter is used before transferring the crop to the central container.

The invention covers five main configurations which are characterized by the crop needed to be harvested:

(A) A universal SPFCH carrier which is design to carry any functional module of SPFCH;

(B) A universal SPFCH, which harvests the crops by plurality of modular robotic arms, that can be mounted in accordance with the harvested crop, and comprising convening system to collect all harvested crops into a main conveying system which directs the crop to a container/basket/box/bin to be accumulated during the crop's harvesting, for further being empty out of the SPFCH when full;

(C) A specific SPFCH-F (fruits) for harvesting pome and stone fruits by using a plurality of modular robotic arms that are configured to reach heights. This special version comprises a hand-like type grabbing device, a hybrid arm with a high maneuverability front section for navigation into the tree's canopy, and a rear section with robust strong mechanical mechanism to tolerate high moments. The hybrid arm comprises a gentle transporter for the fruits, which are transferred to the main chassis that contains automatic limited sorting system, lifts and collapsible bins configured in a magazine that automatically opens and replace full bin by empty one, and lifted down out of the SPFCH-F;

(D) A specific SPFCH-C(Cotton) for harvesting cotton by plurality of modular robotic arms, without ginning, and comprises a convening system for collecting all harvested seed-cotton into a main conveying system or a central vacuum system that collects the seed-cotton from all booms to the main SPFCH-C containers; and (E) A specific SPFCH-G for harvesting and ginning cotton by plurality of modular robotic arms and comprises a convening system for collecting all harvested seed-cotton into a main conveying system that also comprises a drying mechanism, such as controlled hot air or any other heating mechanism, making sure that the harvested seed-cotton arrives dry to the feeding duct of the ginning unit. After the ginning process, the seeds are conveyed to a container to be accumulated, and when full are emptied to an outside wagon/truck. The lint separated by the ginning process is directed by air stream to a bale press accumulator and then pressed to cotton bales. The cotton bales conveys out of the SPFCH by chain conveyor or any other mean (such as pneumatic mechanism).

The SPFCH harvesting device of the present invention comprises at least the following 3 modules/elements:

(1) A main, self-propelled, 4-wheel/4-rubber tracks drive machine-SPFCH/-G, capable of moving relatively fast on roads on its way to the fields while its booms are folded or disassembled and trailed by a platform behind the SPFCH/-G. While harvesting, i.e. in the field, it must be propelled relative slow. It is designed to serve robotic harvesting heads mounted on its booms by providing electricity and computing, air pressure, controlled hot air for drying (in case of cotton) and vacuum to both the robotic picking heads and the transportation mechanism of the picked seed-cotton and the ginning process.

(2) Long booms, aimed to hold plurality of robotic arms, aimed to reach the potential ripped crop, directed by the main computer according to data obtained from the crop-identification optics (CCD/line CCD cameras or other optical detection means such as photodiodes and dedicated optical filters), aimed to detect the potential ready crop to be harvested. It also aimed to hold local vacuum or mechanical mechanism to transport the harvested seed-cotton/other crops, from the plant to the main transportation system that collects the crop from all the robotics units toward the central processing area or accumulation container/s.

(3) A large container(s) for the harvested crop or seed-cotton, aimed to accumulate the crop within the field. The container also equipped with a lifting belt or spiral conveyor mechanism to enable the system to empty the crop from the container to an outside wagon or truck.

In certain embodiments, when harvesting fruits, the SPFCH may further comprise at least one of the following different/additional modules or elements:

(4) A hand-like type grabbing device to gently grab different kinds of fruits, a hybrid arm made of a front-section with high maneuverability and fast robotic arm, for navigation into the tree's canopy toward a recognized fruit, and a rear-section with a robust mechanical mechanism to tolerate high moments of the arm. In certain embodiments, the hybrid arm further comprises a gentle transporter mounted on the arm that follows its movement, for gently moving the fruits from the trees to the main chassis, which is equipped with: (i) an automatic limited sorting system according to predefined quality parameters; (ii) lifts and collapsible bins arranged in a magazine that automatically opens a new bin and replaces a full bin thereby; and (iii) a lift for dropping down the full bins out of the SPFCH-F.

In certain embodiments, when harvesting cotton, the SPFCH of the invention further comprises the following additional modules or elements:

(5) a main transportation and drying system aimed to transport and dry the seed-cotton, harvested by the robotics arms, and transport them, after drying, toward the feeding duct of the gin process;

(6) at least one ginning units in parallel, aimed to separate the seeds from the lint during harvesting;

(7) suitable cotton bale press, aimed to press the lint, after ginning, into compact bale to be transported out of the SPFCH/-G harvester and then out of the cotton field;

(8) optionally, a trailed platform aimed to collect the pressed lint bales and to order them, during harvesting in the field, and to be replaced by an empty platform when full. Such platform may comprise also robotic crane aimed to order the cotton bales on the platform;

(9) optionally, a hydraulic flat tail lift platform aimed to collect the pressed lint bales and to order them, during harvesting in the field, and to be emptied or replaced by empty platform when full. Such platform may comprise also a robotic crane aimed to order the cotton bales or other crops boxes; and

(10) optionally, a manual- or automatic crane to pile the heavy boxes (36) or bales on top of the other and to efficiently order them on the collecting platform;

In case of other crops, such as artichoke, alternative possible trailed platform might trail a platform aimed to collect dedicated boxes of crop, when full, and a crane aimed to arrange the full boxes, during harvesting in the field, and to be replaced by an empty platform when platform is full. Hydraulic flat tail lift platform can be used as well.

The Self-Propelled Cotton Harvester (SPFCH/-G) presented in FIG. 1a, aimed to harvest cotton 1 comprises dedicated high chassis 2, robust wheels or rubber tracks or alike (2b), as common in agricultural machines. Wheels might be propelled by mechanical, electrical, hydraulic or any other high precision mechanism connected to the main power unit 4. Movement of the SPFCH/-G/-F is controlled by a programmable controller and or the central computer 3a embedded in the cabin 3 which will synchronize the speed of the movement, during harvesting, according to signals obtained by the robotic picking arms at the end of each individual picking process.

In certain embodiments of the SPFCH of the invention, each robotic picking arm has its own field of activity thereby enabling other arms to finish picking and enabling movement of the SPFCH/-G/-F. Driving the SPFCH/-G/-F to the field will be made by a human driver while the booms 5 and foldable solar panels 19 are folded, e.g., by hydraulic/pneumatics mechanism or the booms are unassembled and trailed behind the SPFCH/-G.

However, once arriving to the harvesting point, the booms are un-folded by the driver or assembled at it fast and predestined joints, the foldable and extendable solar panels are unfolded and extend to its maximum size and then automatic driving system can, but not mandatory, be activated. The SPFCH/-G/-F is then driven by sensors 37 (FIG. 1a) and guiders mounted on the front of the SPFCH/-G/-F, which keep it in the exact rows dedicated for its driving. By that, the SPFCH/-G/-F becomes fully automatic machine while the driver can just be reported to his cell phone or any other communication devices, when it is required to empty the seed's/crop's container/s or when any failure is reported. At the end of the picking rows, moving the SPFCH/-G/-F to the next stating picking point in the field, can be done by either the driver, if available, or by GPS, programmed prior to the harvesting for every specific field.

In certain embodiments of the SPFCH of the invention, motored and/or motored electric generator 4, mounted on all high chassis modules, provides electricity to all SPFCH's components. Power supply for all components can be obtained by any mobile electrical mean, such as re-chargeable high capacity batteries 2a mounted within the chassis 2 and propelled by the wheels 2b in both sides of the SPFCH/-G or elsewhere on the SPFCH/-G. Gasoline or diesel fueled motored generator can also be used for re-charging the batteries. The central electrical power grid may be used also for night charging, if harvesting is not possible. In case of non-cotton harvesting, night-harvesting is possible due to self-lightening of the SPFCH.

Alternatively, or additionally, foldable and/or extendable solar panels 19 can be mounted on top of the SPFCH/-G/-F for continues charging the batteries or directly to serve the electricity needs.

Figure 7:
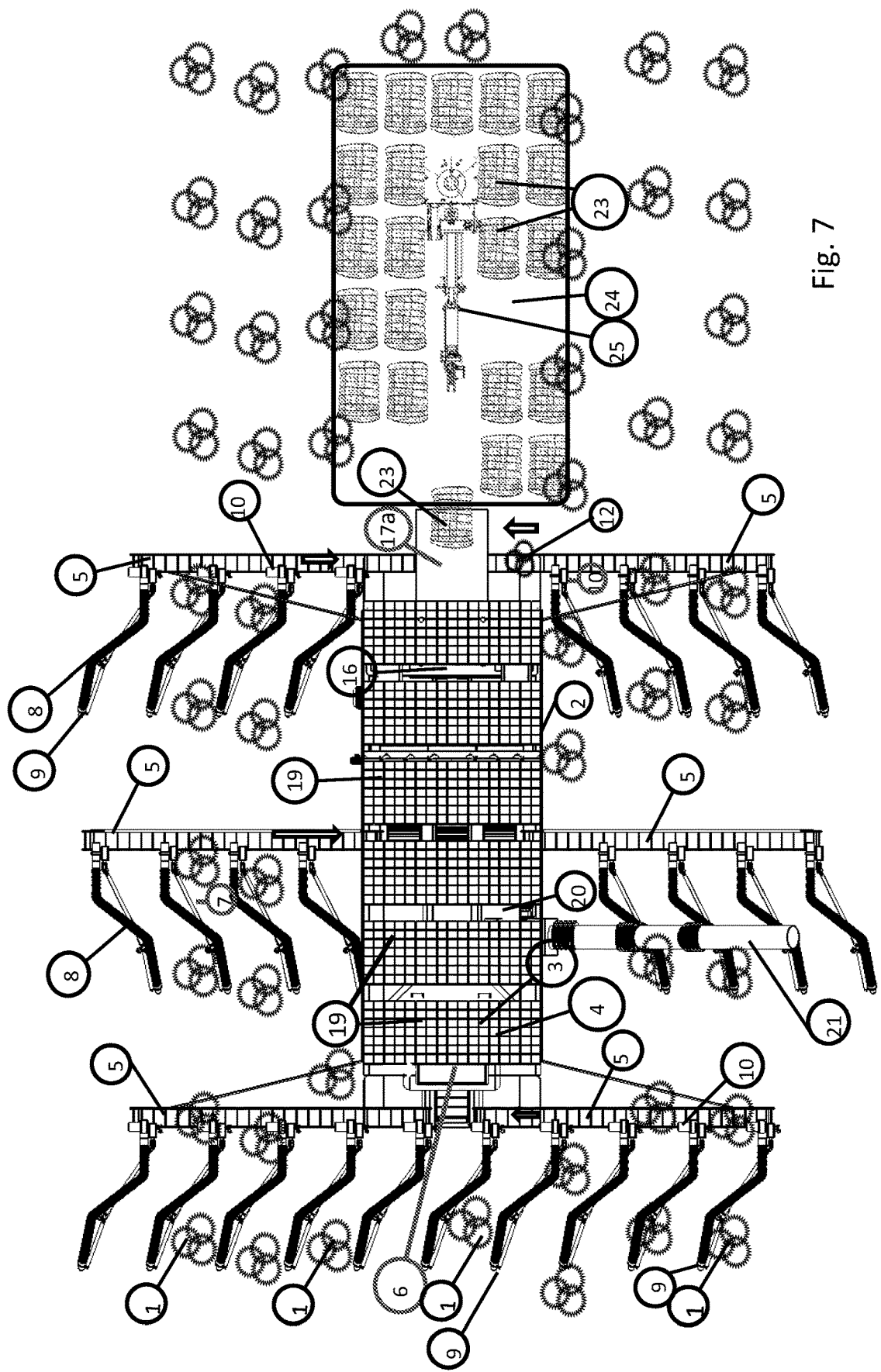
FIG. 7 is a schematic top view of a SPFCH-G within row cotton field, demonstrating the direction flow of material from the vacuumed picking heads to the local conveyor belts into the main transporting belt that feed the gin, including cotton bale trailer and bale sorting crane.
Figure 10:
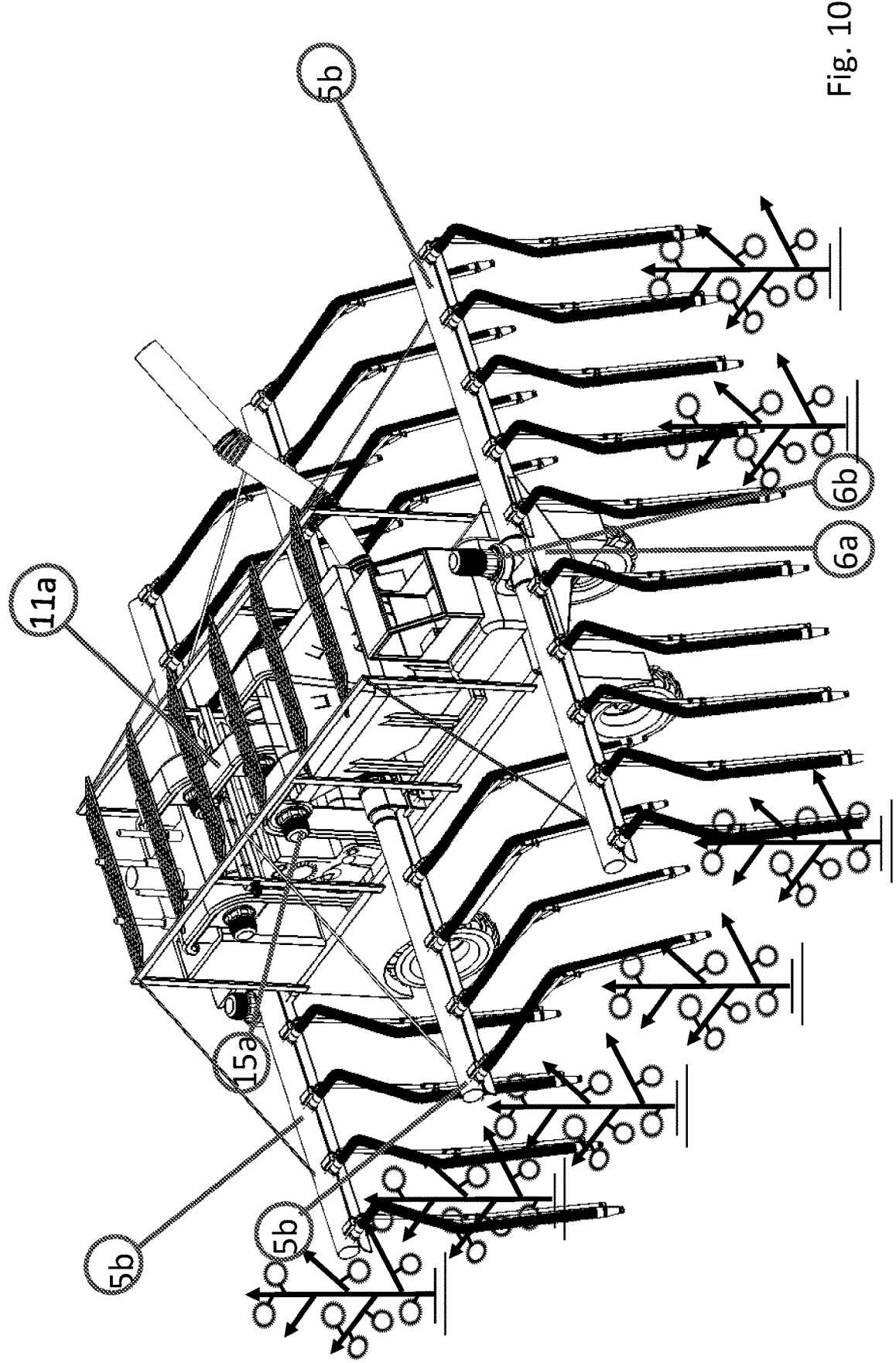
FIG. 10 is a schematic front view of a SPFCH, within row cotton crop, demonstrating the transporting of the harvested seed-cotton by central rigid, but foldable, pipes main vacuum system toward the feeding hopper of the gin.
Figure 11:
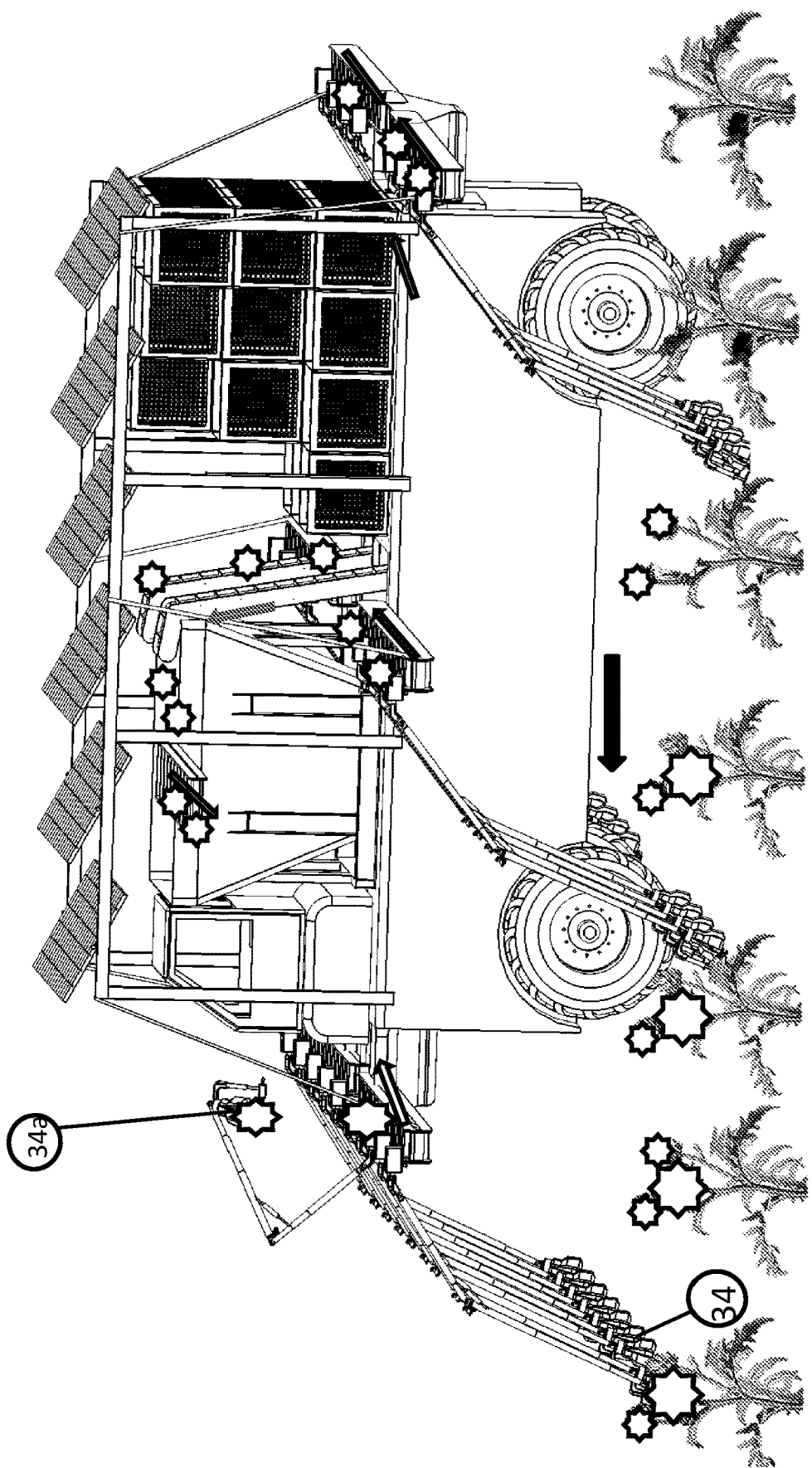
FIG. 11 is a schematic side view of SPFCH, version aimed to harvest heavier crops such as artichokes and alike, within a row field, the module for harvesting only, detailing the fact that this version do not comprise vacuum hoses. The robotic arms are designed to hold the crop during picking by gripper, and automatically to cut its stem and to bring it gently on the local transporting belt. Arrows demonstrate the flow of the harvested crop from the plant to the SPFCH and out when the containers are full. One robotic arm demonstrates bringing harvested good to the local transporting belt.
Figure 12:
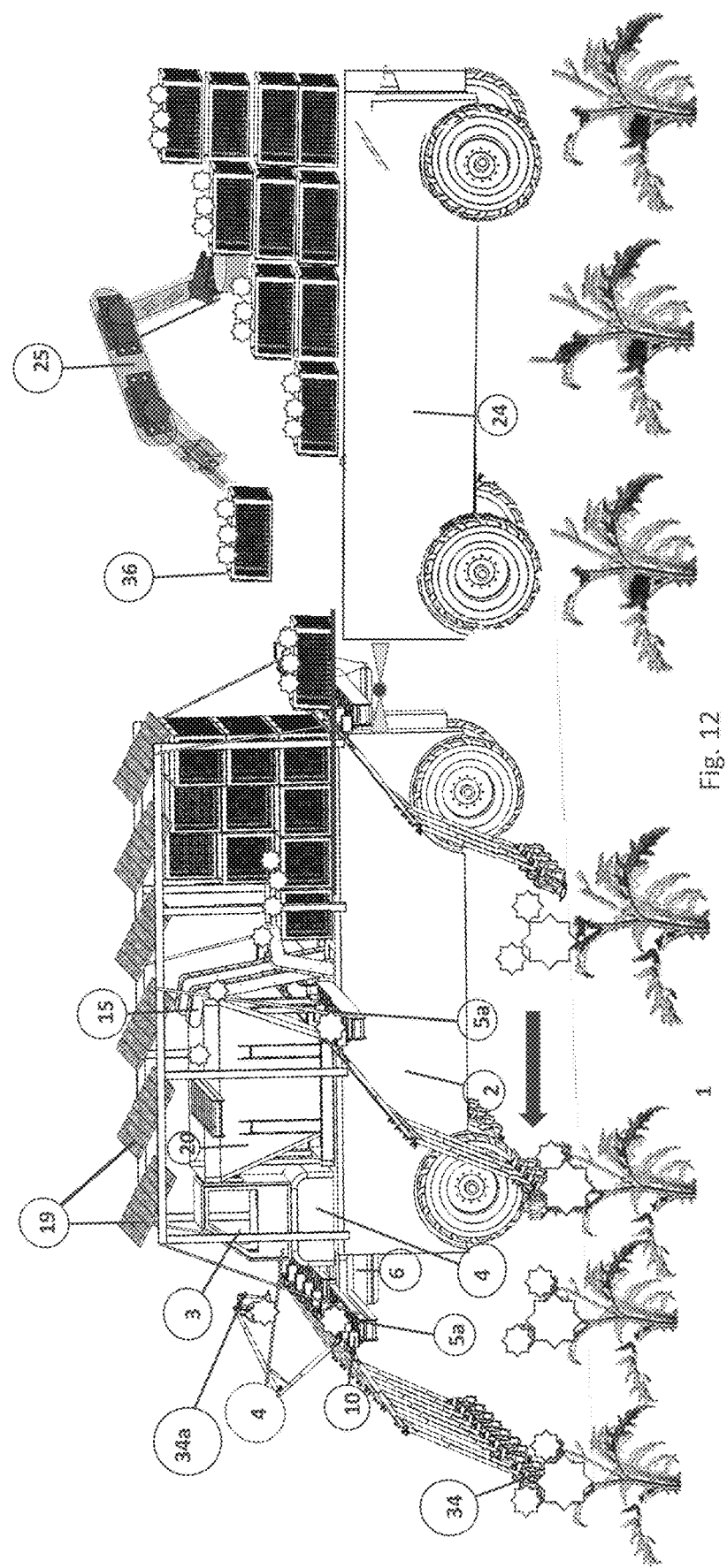
FIG. 12 is a side view of a SPFCH of the invention in an artichoke field or alike, demonstrating plural amount of grippers and cutting picking heads, full boxes trailer, box organizing robotic crane and solar panels on top.
Figure 13:
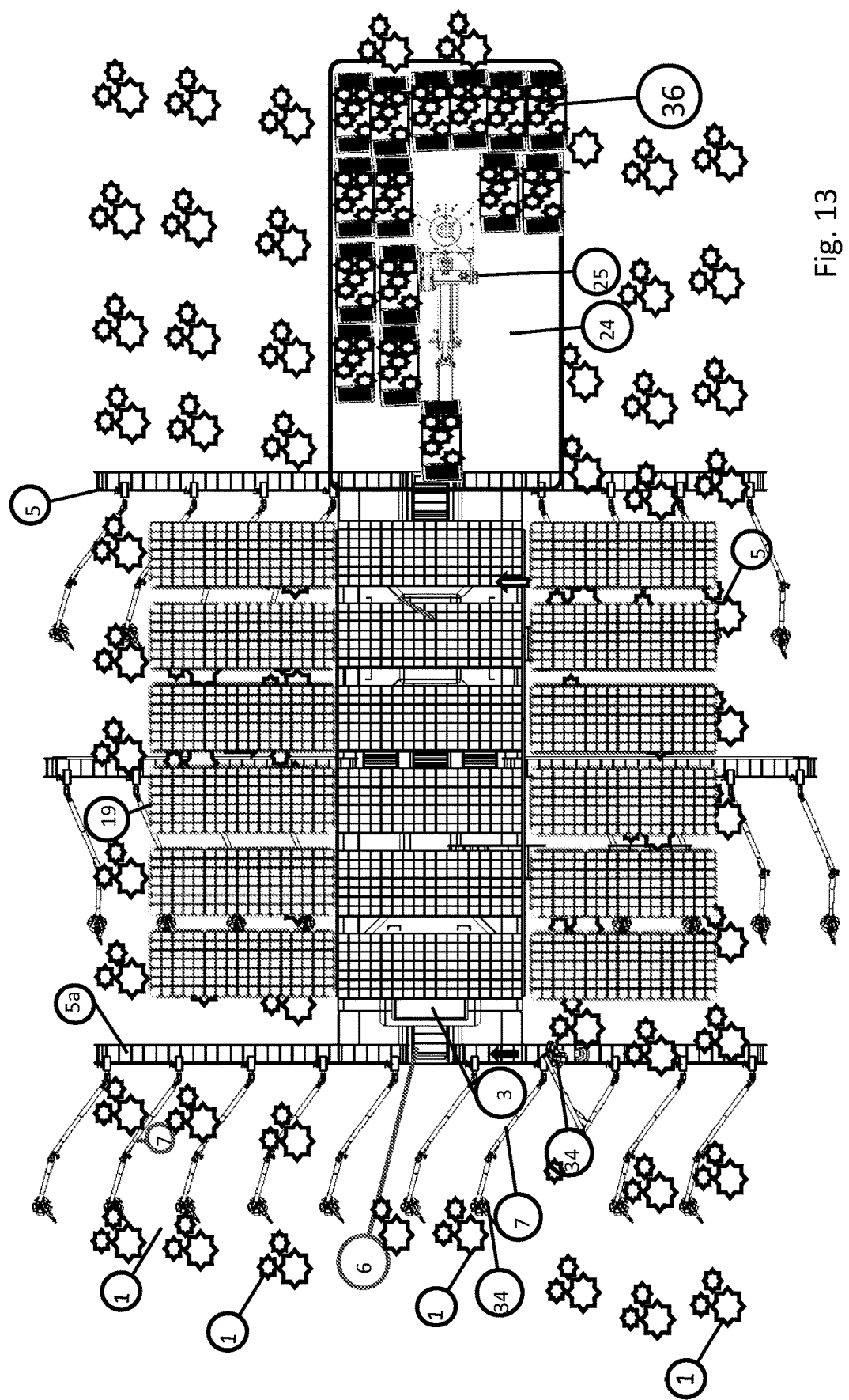
FIG. 13 is a schematic top view of SPFCH, for harvesting artichoke and alike, within rows of artichoke field, detailing the position of the booms, the different transporting mechanism and elevators and containers, power unit including the unfolded and/or extendable solar panels, and all the mechanical needs to transport the filled boxes from the SPFCH toward the trailer (the option of hydraulic tail lift is not shown) that comprises an organizing crane, and the ability to hang plurality of picking robotic arms either in the front rear and side of the SPFCH.
Figure 14:
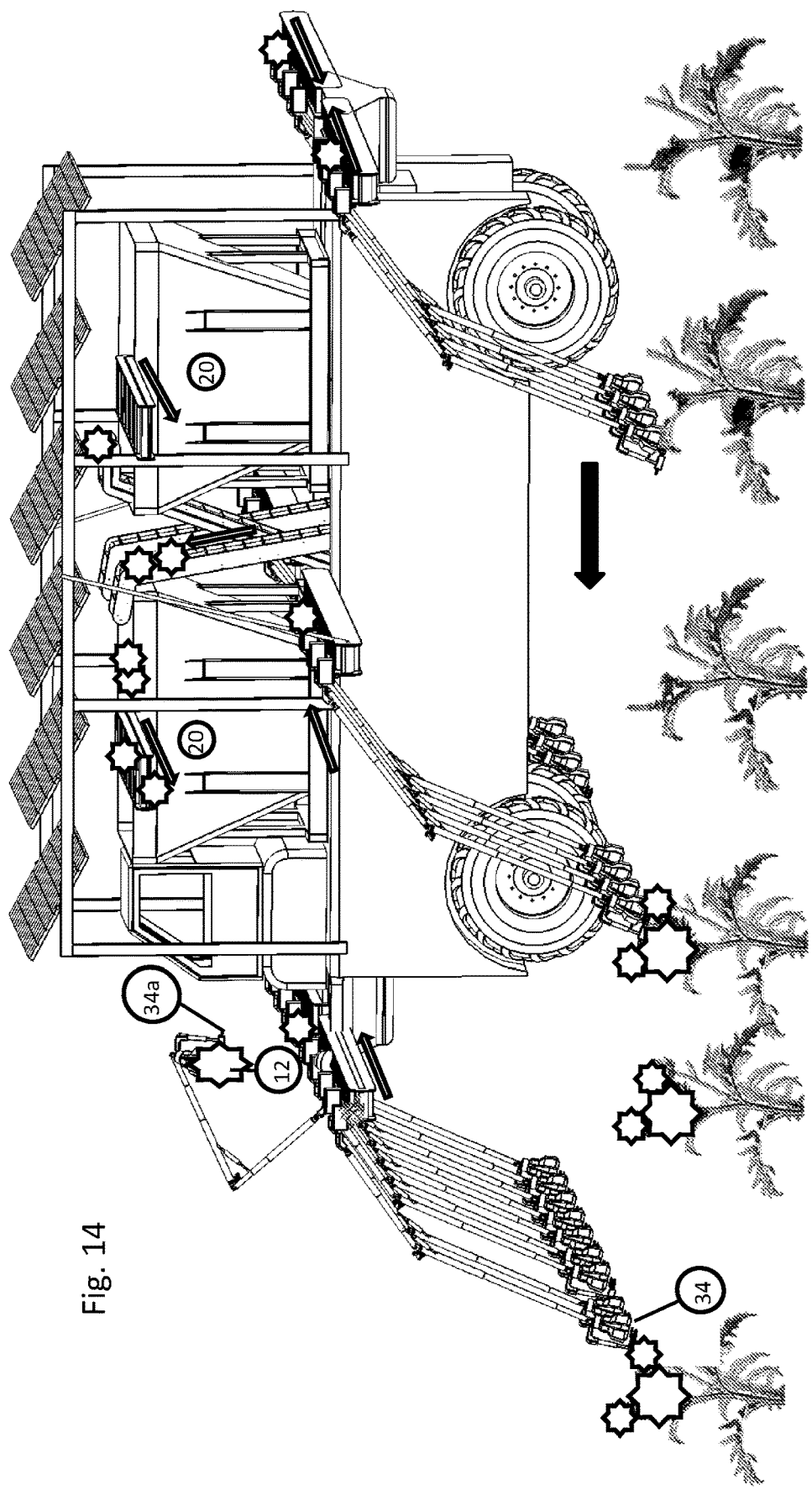
FIG. 14 is a schematic side view of SPFCH version aimed to harvest heavier crops such as artichokes and alike, within a row field, the module for harvesting only, detailing the fact that this version do not comprise box and trailer but just two containers to be empty when full.
Figure 15:
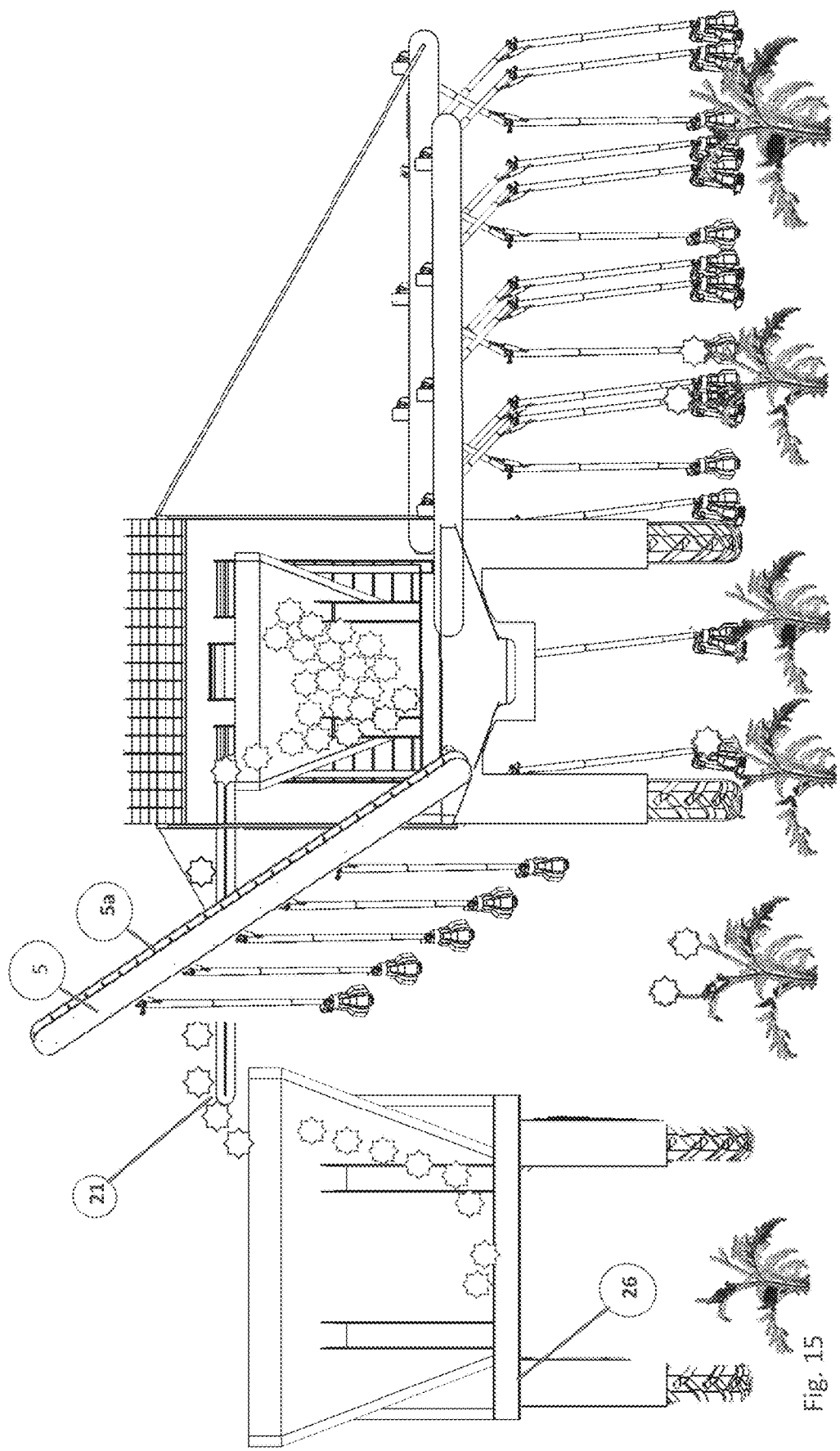
FIG. 15 is a schematic rear view of a SPFCH, demonstrating emptying a crop, e.g. artichoke, from the SPFCH container to a separate wagon in order to proceed with harvesting. It also demonstrates that booms can be folded if needed, to allow accesses to the wagon and also for driving the SPFCH from one field to another.

In certain embodiments, the SPFCH of the invention also comprises a big container (20) to contain the harvested crop or the cotton seeds 22 [depend on the SPFCH or SPFCH-G or bins (SPFCH-F) configuration] accumulated while harvesting, a spiral or belt conveyor 15 will be used to lift the crop or the seeds, after ginning, to the seed's container, a second conveyor 21 will be used to empty the crops/seeds out of the SPFCH/-G's container. The SPFCH/-G also comprises at least one hanging boom 5, which hangs the robotic arms 7 and its attached vacuumed hose 8 used for picking the crop and can be installed in the front, in both sides of the SPFCH/-G and in its rear side (see FIGS. 7 and 10) depend on the harvesting capacity needed.

In certain embodiments, the SPFCH/-G further comprises some kind of conveyor belts for transporting the crop. As illustrated in the figures, in certain embodiments the SPFCH of the invention comprises a main flat belt/flat chain conveyor 5a that collects all the single crops harvested at a point adjacent to the picking position, and transport it to the main transporting system 6 located within the SPFCH/-G/-F chassis. The main transporting system transfers the crop from all booms, regardless its position, to a lifting belt 15 which lifts the collected crop either to a container/basket/box in case of SPFCH, or to a feeding hopper 13 of the gin stand/s in case of SPFCH-G. At the case of SPFCH-G the lifting conveyor 11 needs to be covered by heat resistant duct to enable the cotton to be dried during lifting the seed-cotton, in controlled hot air duct, toward the hopper 13 of the gin stand/s, since the ginning process requires dry seed-cotton for best performance.

Figure 6:
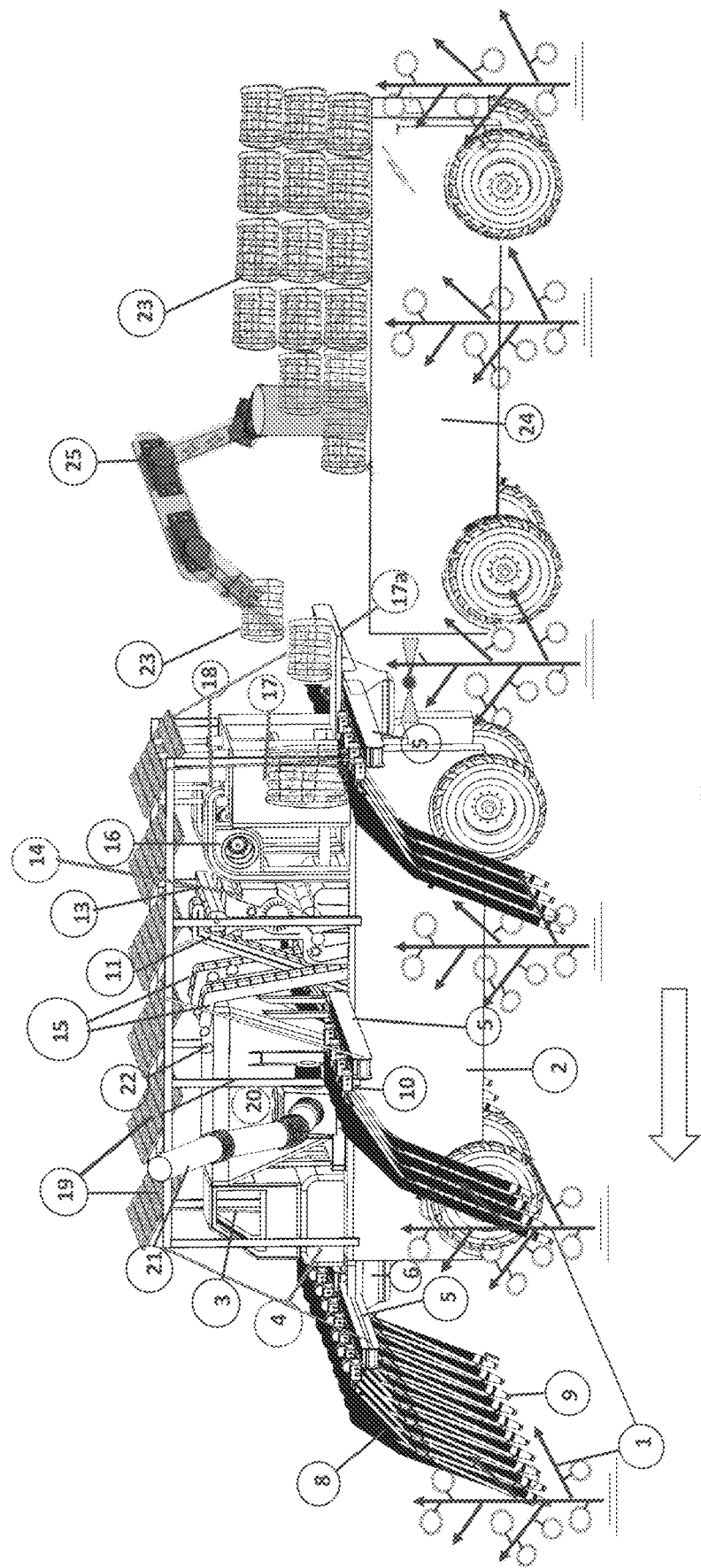
FIG. 6 is a schematic side view of cotton and ginning module of a SPFCH-G of the invention within a row cotton field, and the trailed platform for collecting the lint bales and the ability to hang plurality of picking robotic arms in the front, rear, or side of the SPFCH.
Figure 9:
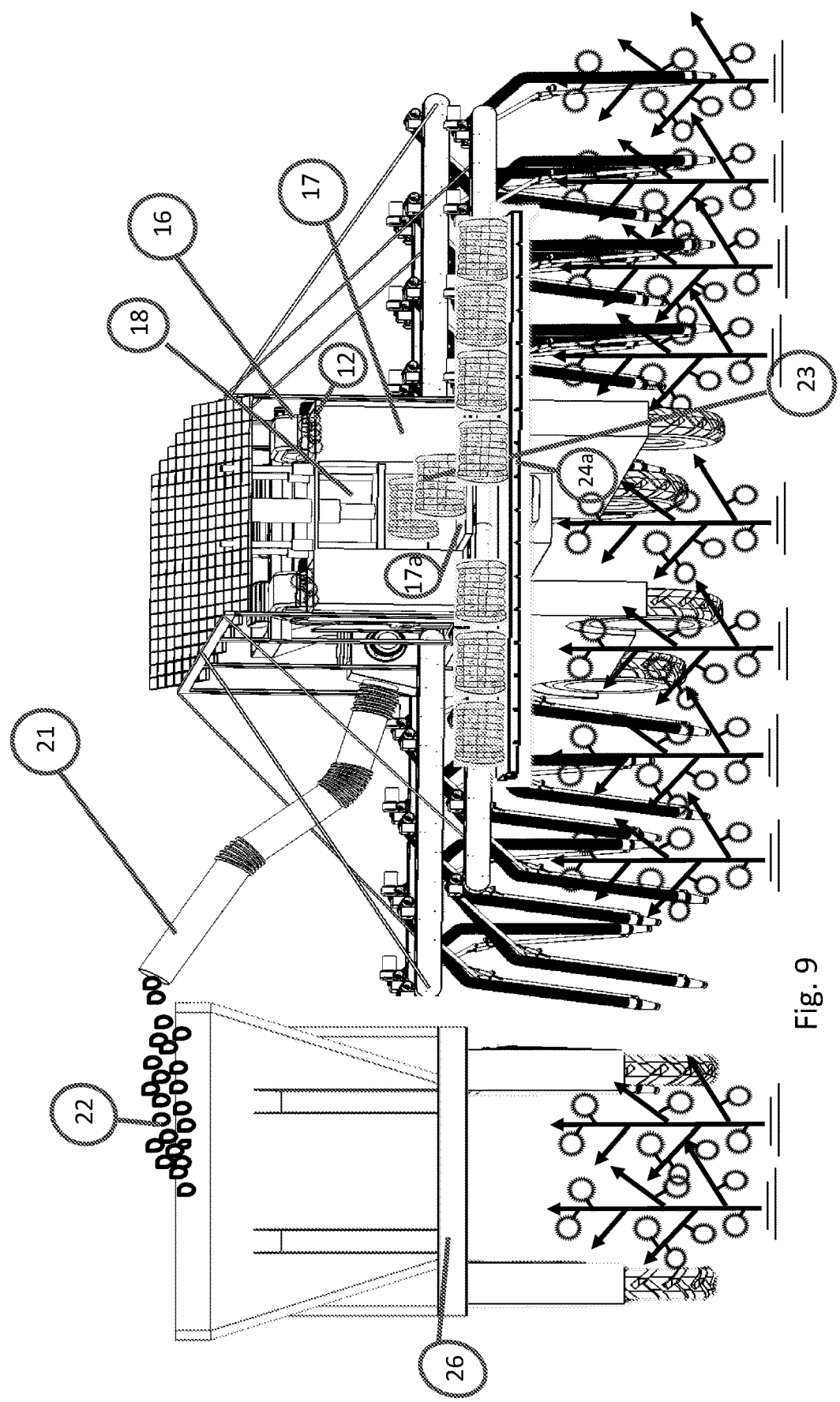
FIG. 9 is a schematic rear view of the cotton and ginning module of a SPFCH-G of the invention within a row cotton field, detailing the position of the booms, the conveying hose for emptying the cotton seeds from the SPFCH-G container to a separate wagon and also the output of the cotton bales from the bale press onto a flat tail hydraulic lift.

In the case of SPFCH-G, the amount of gin stand/s 14 installed on the SPFCH-G chassis, depends on the capacity of harvesting. The bigger the capacity required the wider the SPFCH-G will be designed. As the width of a standard roller-gin is about one meter, any amount between one to four ginning stands 14 can be considered as reasonable to be installed on the SPFCH-G. However, the present invention does not limit the number of gin stands or the gin capacity. The invention is not limited to install roller-gin only. Saw-gin runs at much higher ginning rate then roller-gin so future customers might order either saw-ginning or roller-ginning, depend on their cotton varieties and needs. Bale press 17 and its accessories (e.g. oil pump and bands tightening device—not detailed since commercial available) and lint 12 feeder 16 are common need for both the saw-ginning and roller-ginning. The bale 23 produced by the baler 17 (FIG. 6) after tightening, (manually or automatically) will be pushed by designed mechanism and will slide on its opened door 17a (FIGS. 6, 7 & 9) or chain belt and released, toward the SPFCH-G, most probably, but not limited to, a flat platform 24 (FIG. 6) that will be trailed after the SPFCH-G, in order to collect the lint bales, until arriving to an unloading point (out of the field) in which the bales will be transfer to trucks and then out to a warehouse.

Figure 8:
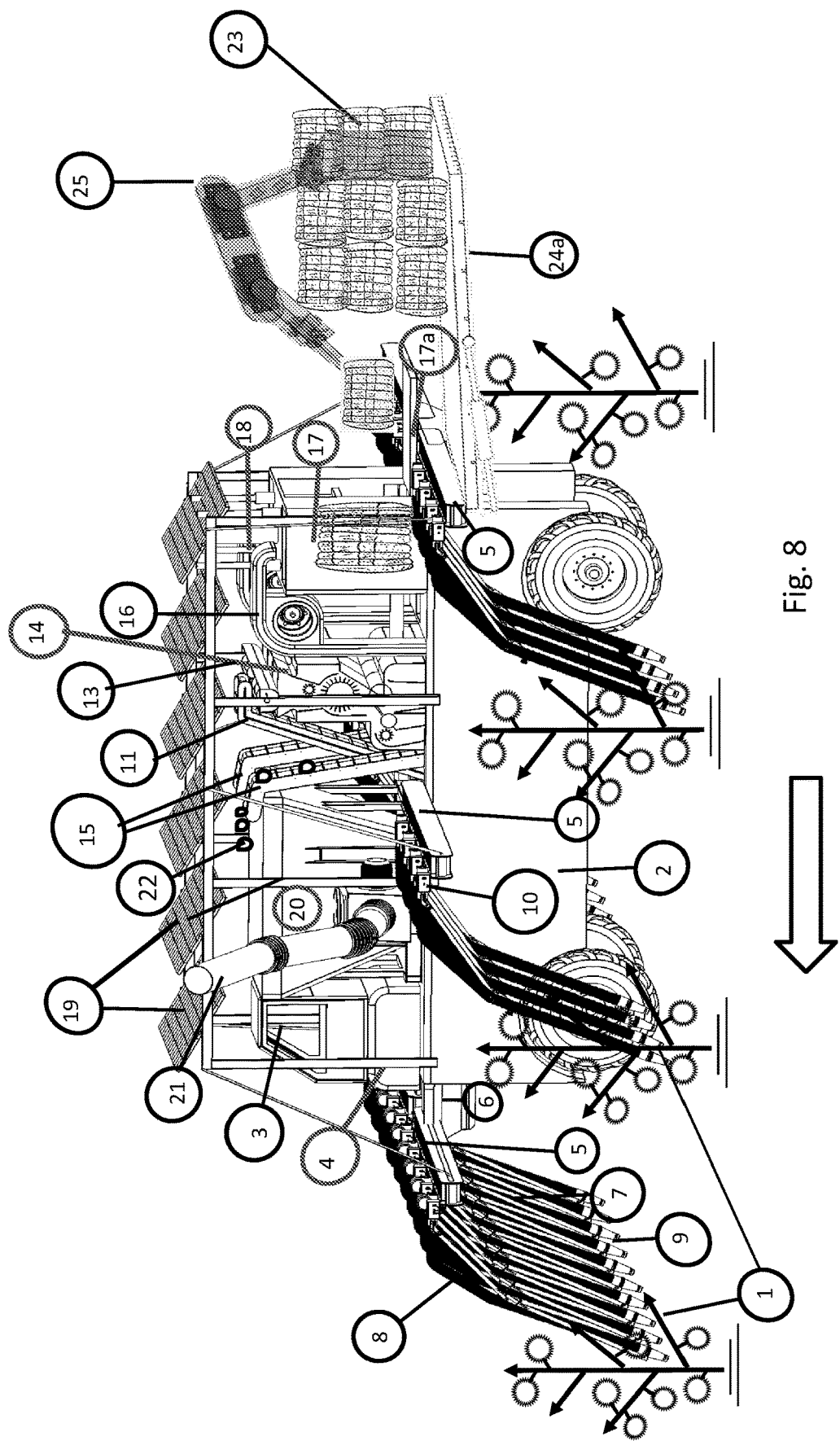
FIG. 8 is a schematic side view of a SPFCH-G within row cotton field, demonstrating the alternative option of a flat hydraulic tail lift and its bale sorting crane instead of trailed platform.

A flat hydraulic tail lift 24a (FIG. 8), mounted on the rear side of the SPFCH/-G, and might be an option of replacing the trailed platform in order to avoid the need of using a trailer.

Figure 17A:
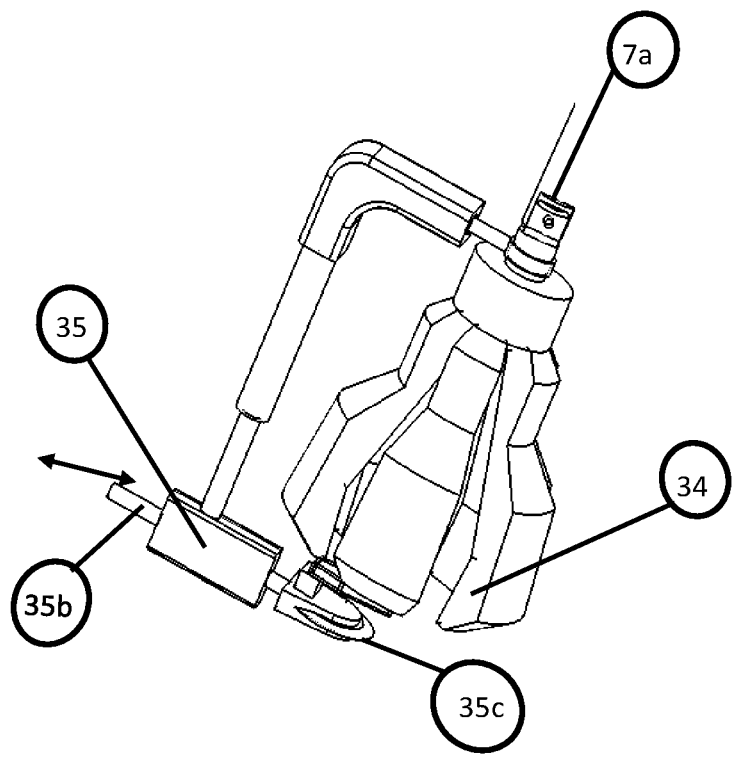
FIG. 17a is a zoom drawing of a gripper and cutting device mounting on each robotic arm aimed for harvesting artichoke and alike crops.
Figure 17B:
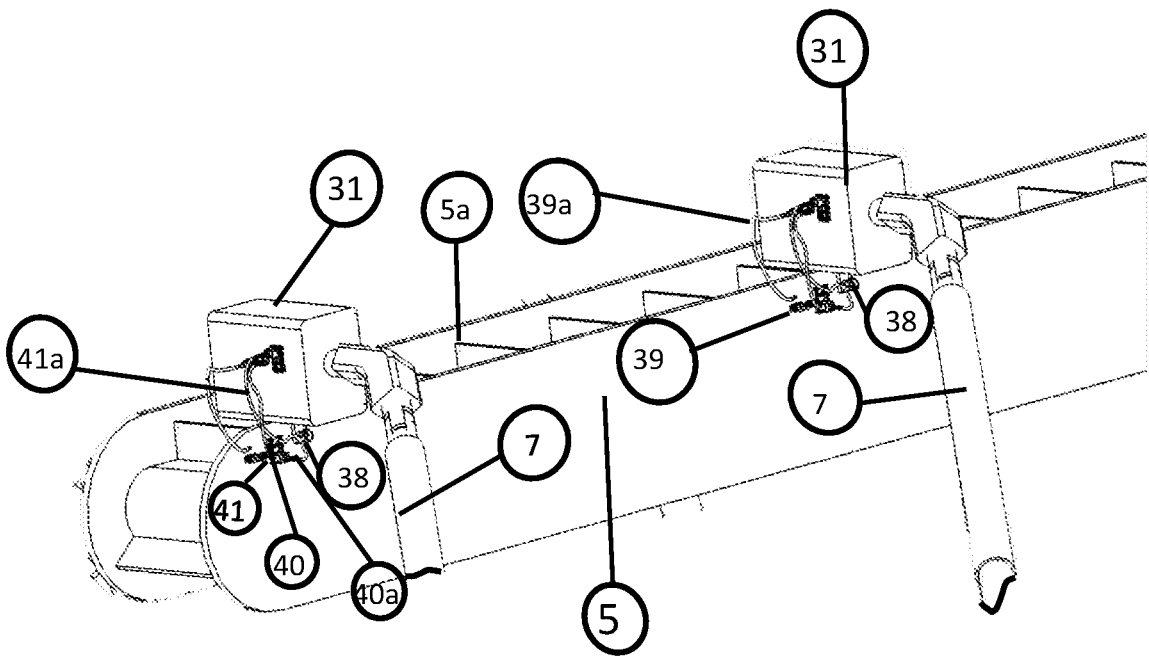
FIG. 17b is a zoom drawing of a pre-designed modular hanging point on the booms.

In certain embodiments, each one of the crop's picking heads of the SPFCH of the invention comprises the following components: Robotic arms 7 comprising at least one robotic motor & joint 31 (FIGS. 16&17) to enable vertical movement, one joint 7a (FIG. 16) to enable horizontal or up to 360° movement so that the arm will be able to access a single or multiply crop in one position or to bring the crop to the conveyor belts on the boom in the other position 34,34a (FIGS. 11-14) in case of gripper, or in case of orchard's crops, to bring a fruit from the picking point on the tree (1) to the arm catcher (5d) (FIG. 18a). The modular joints 31 (FIGS. 16 & 17) can be mounted at a pre-designed points on the boom at an order suitable for the specific crop, according to the amount of rows needed and the capacity of harvesting. Each pre-designed hanging point comprises at least secured hanger 38 (FIG. 17b), which will avoid disconnecting the arm from the boom, electricity cord 39 and its connector 39a, ID based data cable 40 and its connector 40a wired or wireless by means of Bluetooth or local WiFi installed on the SPFCH and air pressure tube 41 and its connector 41a to enable any kind of the SPFCH robotic arm to function regardless of its mounting position.

The robotic arms might be mounted on the front, rear or side booms according to the crop and the capacity needed. The outer part of the robotic arm (the last part on which the vacuum hose ends with the picking device 7a (FIGS. 16a & 16b) the one close to the crop) (FIG. 17a) might comprise enlargement mechanism to enable the arm to access a crop hidden inside the canopy. A possible laser or radar rangefinder 28a (FIG. 16c) mounted within the crop-identification optics 28 and the CCD camera 27 in front of the robotic arm 7 might guide the arm to the hidden crop within the canopy.

For the lightweight crops, such as cotton or okra, a vacuum hose 8 is attached to the robotic arm 7 and its front side 9 is directed toward the ripped crop 12 attached to the plant 1, by the robotic arm 7a. The other side of the hose 8 is connected to a local small vacuum blower 10 suitable to suck one boll or small cluster of bolls, efficiently and transport it to the transporting belt 5a mounted on the boom 5. The blower is powered by wires connected to the modular connectors 39,40 installed on the joint 31 mounted on the boom 5.

In another alternative, instead of having local small vacuum sources 10 each of the vacuum hoses 8 is mounted in one end to the robotic arm, for picking the crop, and in the other side to a central vacuum duct 5b (FIG. 10), which is connected to a central big vacuumed system 6b (FIG. 10) located on the SPFCH-G. The outlet of the big vacuumed system 6b is connected to a duct that direct the seed-cotton either to the main container's lift 15a (FIG. 10) in the case of SPFCH without gin or to a heated duct 11a (FIG. 10) in the case of SPFCH-G.

Figure 24:
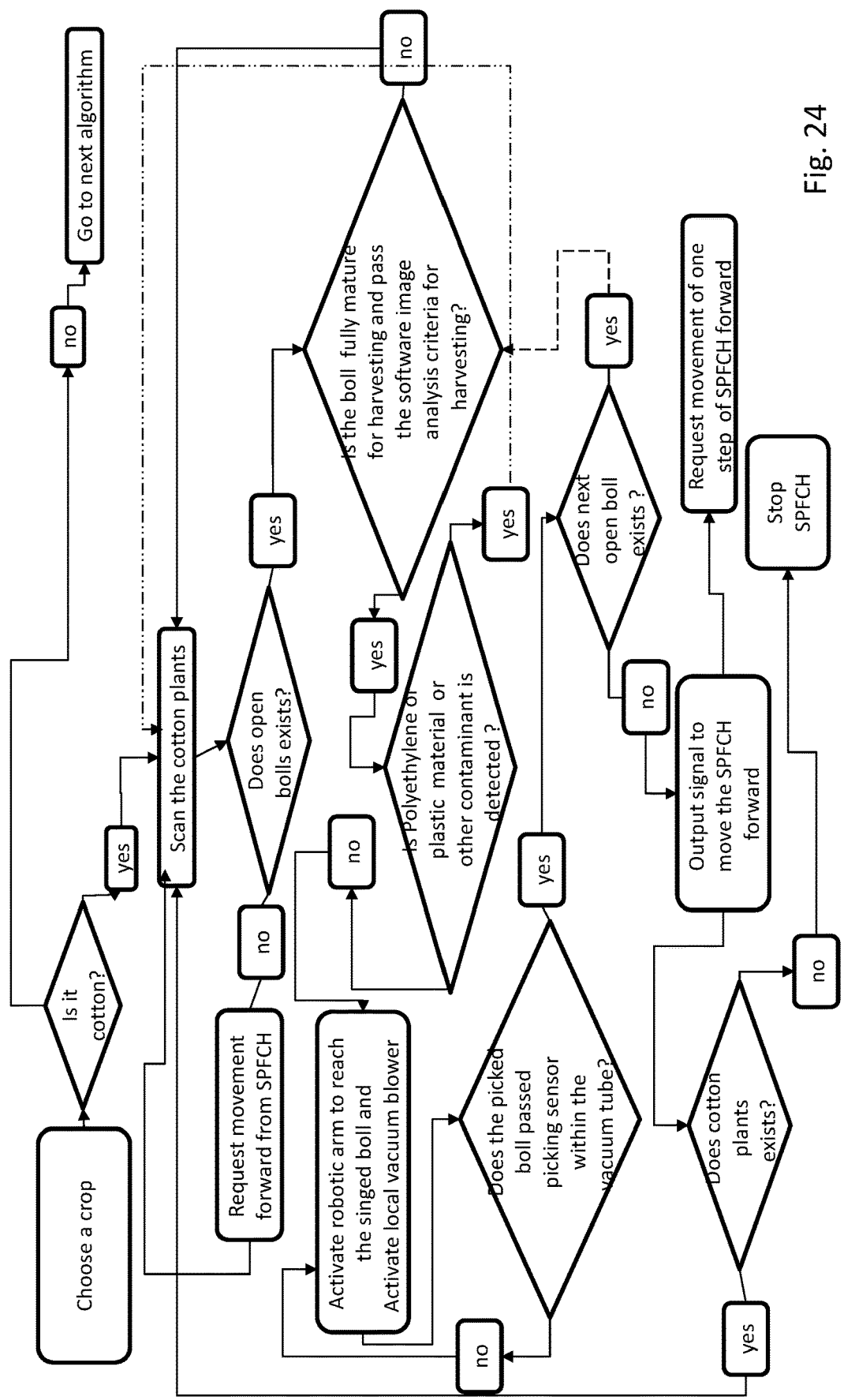
FIG. 24 is a basic flow chart of possible algorithm for operation of image based harvesting of cotton utilized by a SPFCH-G of the invention.
Figure 25:
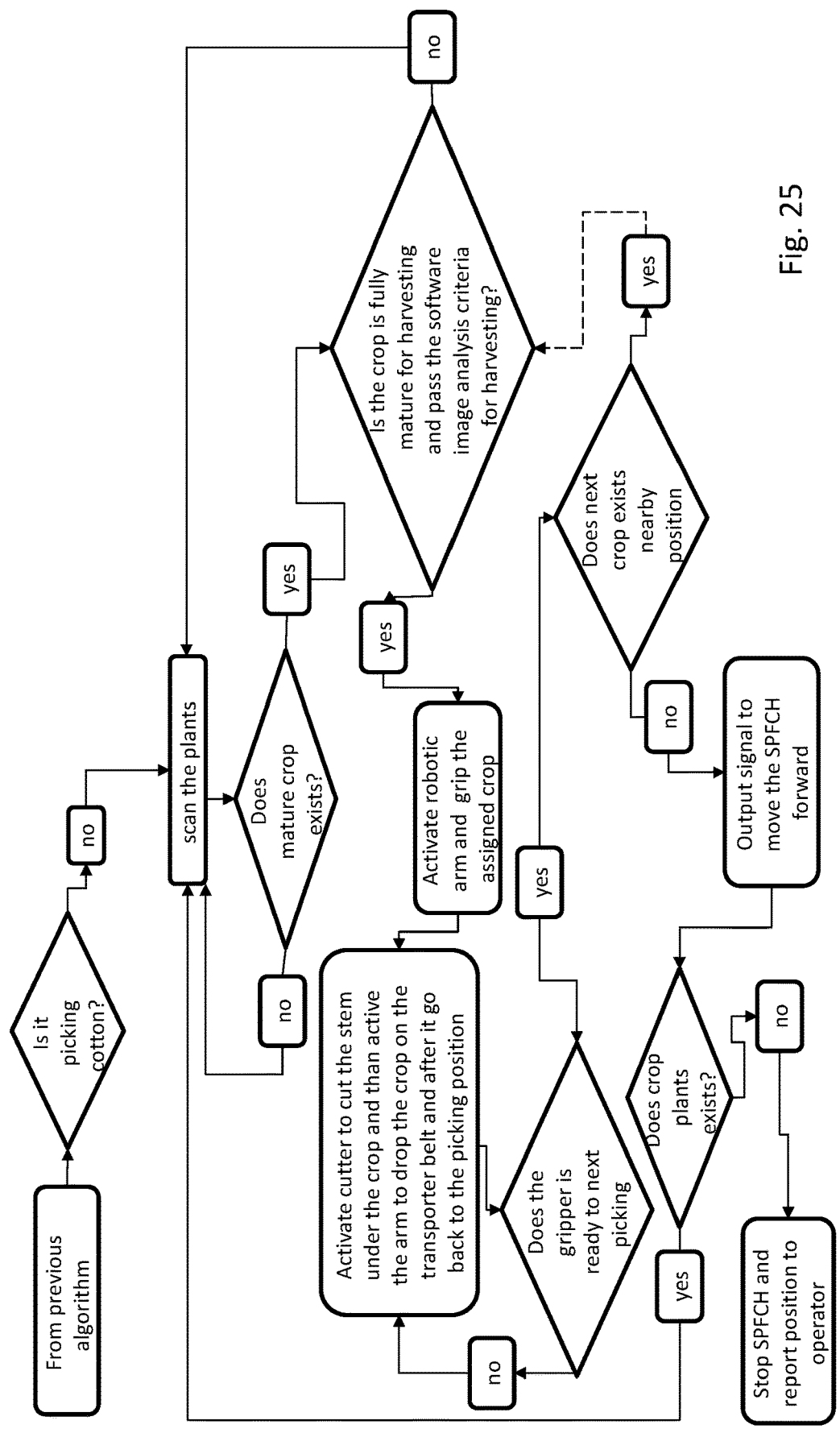
FIG. 25 is a basic flow chart of a possible algorithm for operation of image based harvesting of crops other than cotton for utilizing by a SPFCH of the invention.

Optical device/crop-identification optics for picking 27,28,28a (FIG. 16) are mounted on any place of the robotic arm and comprise tiny CCD colored or B&W camera supported by optical filters 27 illumination of any kind such as IR, UV, visible-light, laser or else as best suitable for detecting any crop 28. Possibly, a laser/radar rangefinder 28a mounted in the cockpit or elsewhere on the SPFCH or near the camera. The optical unit is protected by transparent cover to protect the optics. All the CCD cameras are connected to the main computer 3a by wires or wireless or by Bluetooth or any local WiFi or communication system installed on the SPFCH 2. The computer uses a specific algorithm (general possible flow chart is presented in FIGS. 24 & 25), for each crop, to enable recognition of the ripped products in oppose to the non-ripped crop that need to be harvested at a later round. For cotton, the software is also designed to detect foreign materials, such as plastic bags, by color, reflection or wave length absorption. Such detection causing the robotic head to skip such boll and not letting the foreign material to be harvested and contaminate the seed-cotton and later the lint.

In case of high-weight crops, such as artichoke, the robotic arms comprise a gripper 34 (FIGS. 16a & 17a) and automatic cutting device 35 mounted near the gripper to enable the robotic arm to hold the crop (e.g. artichoke) and then to activate the cutter device 35b,35c to decapitate the crop in order to enable the arm to transfer it to the transporter and then to the container. Any arrangement of cutting device such as movable knife, Open/close scissors or laser burning types might be used as well, depend on the crop harvested.

The booms 5, on which the robotic arms 7 are being mounted, can be manufactured in different length or in a length-shift able capabilities (e.g. telescopic bars 7a, FIG. 16a), so as to be adapted according to the crop being harvested, can be made of any material such as metal, aluminum, composite resin materials, etc., all foldable and robust enough to move within the crop's canopy while being able to move the SPFCH from field to field.

Figures 26A, 26B:
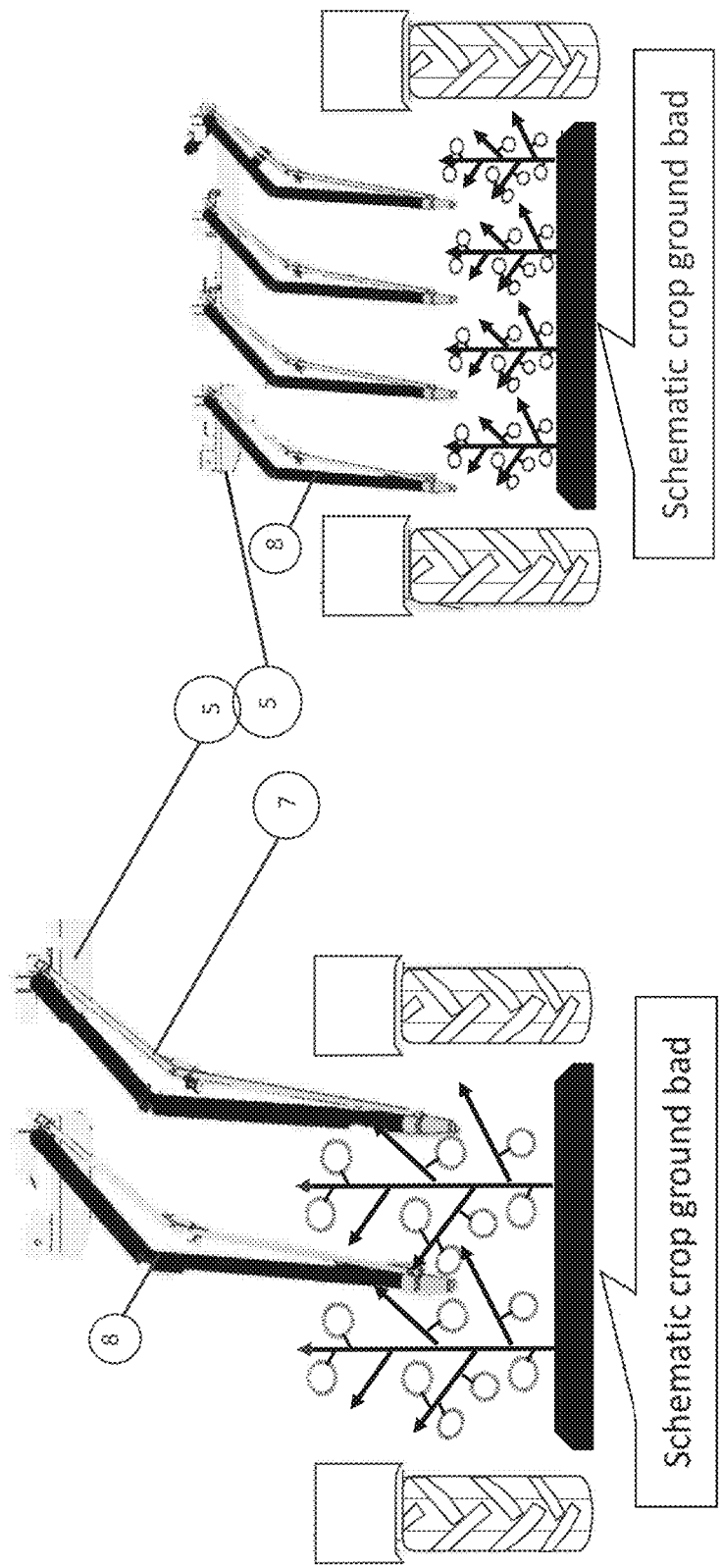
FIGS. 26a-26b demonstrates mounting robotics arms for cotton harvesting at low and high density of plants.

The modular design of the booms 5 enables to hold plurality of modular robotic arms 7 customized according to the crop and its plants density on the growing rows, within a bad, as practice in each country or in each specific agro technical practice (see FIG. 26a for low-density and FIG. 26b for high-density). Some grow a crop in wide rows (about one meter between rows—option A) and therefore relative high plants will grow (FIG. 26a) and many bolls will need to be picked, while others might plant up to six rows on a bad (mainly in cold countries) and therefore low plants with few bolls only will fruit on each plant (FIG. 26b). Therefore, the amount of the modular robotic arms 7 might change from country to country (and within different region within a specific country) and from any SPFCH, depend on the harvesting capacity and the agro-technics in the country. The booms 5 might be mounted at the front of the SPFCH, at both sides or in rear side, all depends on the harvesting capacity needed, since, for example, in the beginning of harvesting season the capacity might be lower than the next harvesting periods.

Furthermore, modularity of the SPFCH enables it to switch from crop to crop at different seasons, (not applicable to the cotton SPFCH-G), by just changing the specific mechanical module and its picking algorithm and the positioning of the robotic arms or its type (from grippers to vacuum and back) according to the harvesting need. Even mounting different booms or switching to orchard module is possible.

Figure 2B:
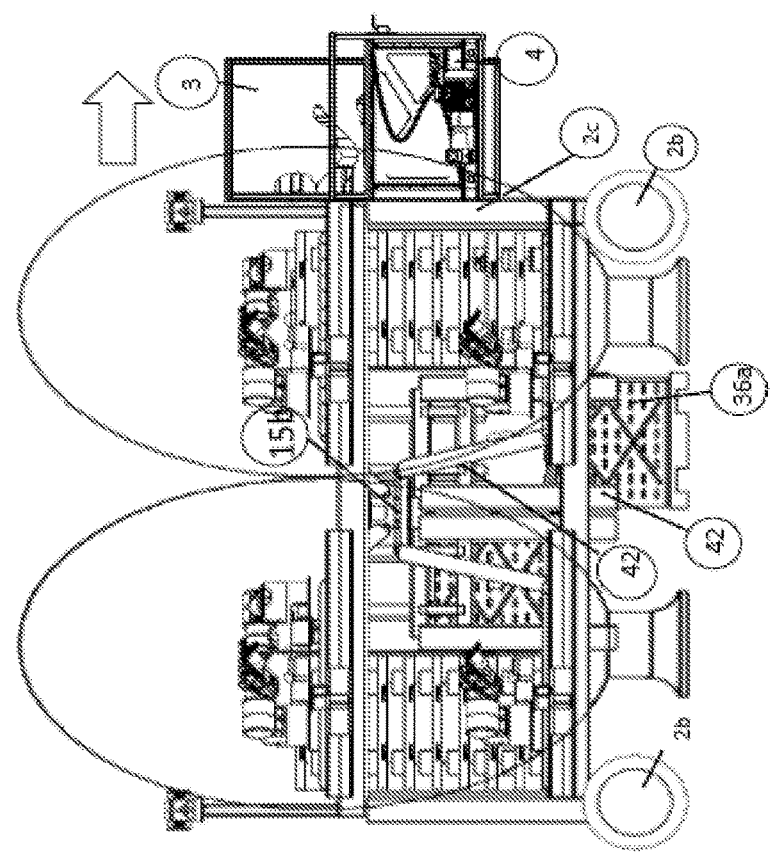
FIGS. 2a-2b are schematic side views of a SPFCH's module aimed for picking tree's fruits in which the robotic arms are installed in 2 levels in order to cover the whole range of the tree's height and its specific components for orchards.
Figure 2A:
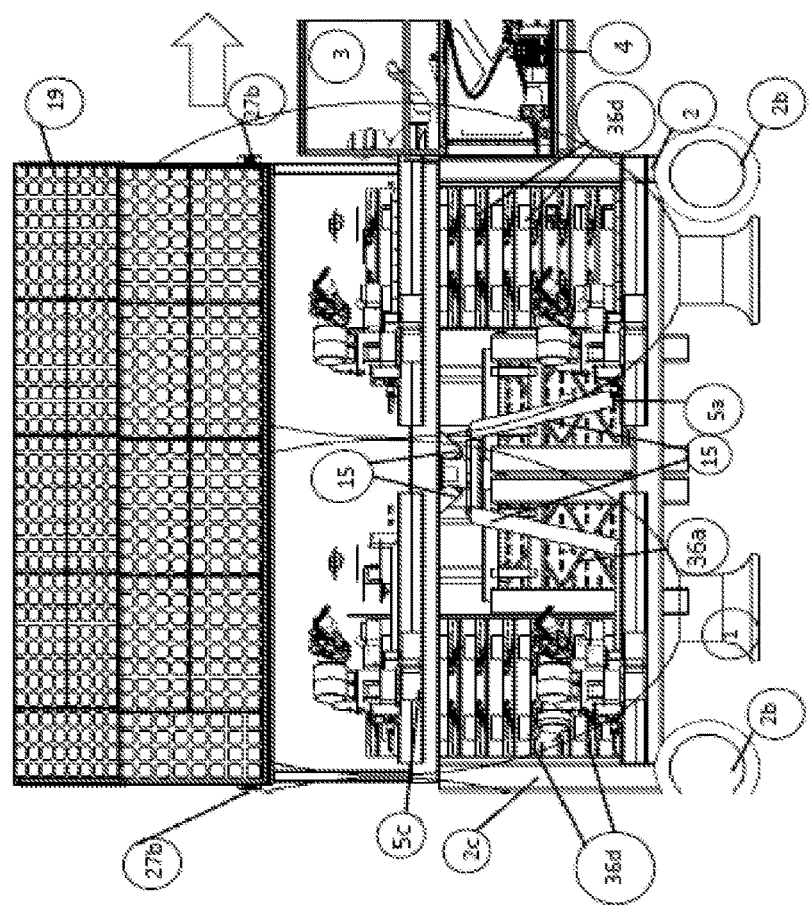

In case of SPFCH-F, for picking or thinning fruits, the chassis needs to be designed in two levels as shown in FIGS. 2a, 2b and 3a, to enable the robotic arms to reach, in parallel, both low and high fruits. FIG. 2a is a side view of such a configuration showing the chassis 2; the wheels 2b; the cabin 3 and the power unit 4; the fruit transporting elevators 15 from both the upper and the lower levels, transporting the fruits to a rotating round carousel 15b (see also FIG. 3c), which collects and buffers the stream of fruits coming from all transporting belts (of one side) and feeds the sorting and cull diverter station 15c, which conducts automatic quality inspection (commercial available) before transporting the fruit to its final destination which is bin 1 or bin 2, according to the fruit's quality. In this view, two stations of, e.g., 10 folded bins 36d within their magazine 2c (see also FIG. 5a) can be seen, and two open bins 36a in their picking position. Collapsible bins can be made of any plastic oriented materials, such as aluminum or tin, but also can be semi disposable if made of cardboard. Camera and illumination means 27,28 located on the robotic arm 7e can also be seen. In this exemplified configuration, four robotic arms (see detailed drawing in FIGS. 18a and 18b) are installed in each side of the SPFCH but the number of arms is not limited according to the current invention and can be determined according to the harvesting capacity needed.

FIG. 2b shows one of the bins 36a lifted down when full.

FIG. 3a is a front view of the invention showing how the SPFCH-F harvests on both its sides, emphasizing the chain belts 43 that constitute part of the automatic mechanism of the bin's opening of the collapsed bins within its magazine.

FIG. 3b is a bottom view showing the elevator 42 and a linear slider 5c (see details at FIG. 18b), on which the hybrid arm is mounted, in order to enable the whole hybrid arm to move to its best picking position as dictated by the main control system before and during the picking process.

FIG. 3c is a top view of the SPFCH-F showing the two bins 36a at their picking position; the two magazines of fold bins; the buffer carousel 15b; the fruit sorter 15c; and the inner transporters 15d that transports the fruits into the bin without dropping.

FIG. 4a illustrates the process of folding a bin. Notably, in this particular configuration the SPFCH uses a very specific configuration of collapsible bins. However, the invention covers any other collapsible bin configuration. As illustrated in FIG. 4, first, two of the side walls are pressed against springs 36f; once the walls are in horizontal position, the other two walls are collapsed against their own springs 36e into the final fully fold bin 36d configuration.

FIG. 4b demonstrates the process of automatic unfolding a collapsed bin 36d by holding a pile of bins with a pneumatic pin 42b and automatically releasing the holding pin 42a at the bottom bin. This cause the bin to automatically unfold thanks to its own springs into an open bin configuration ready for picking. At this stage the chain belts 43 are automatically activated to move the open-bin into its picking position by pushing an elevator tray 42d.

Figure 5C:
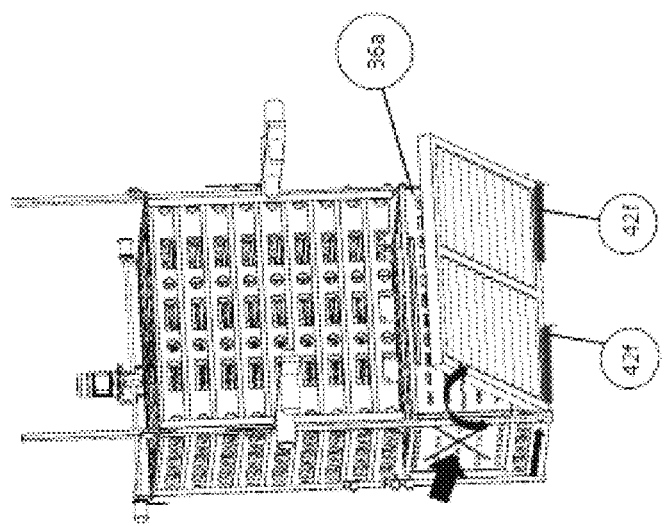
FIGS. 5a-5C are isometric views of an automatic bin exchanger.
Figure 5B:
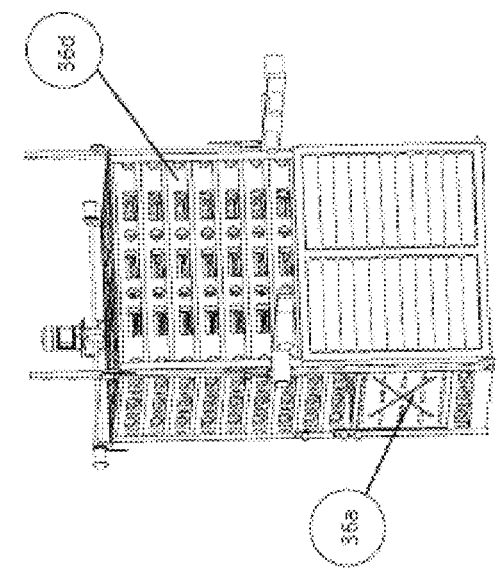
Figure 5A:
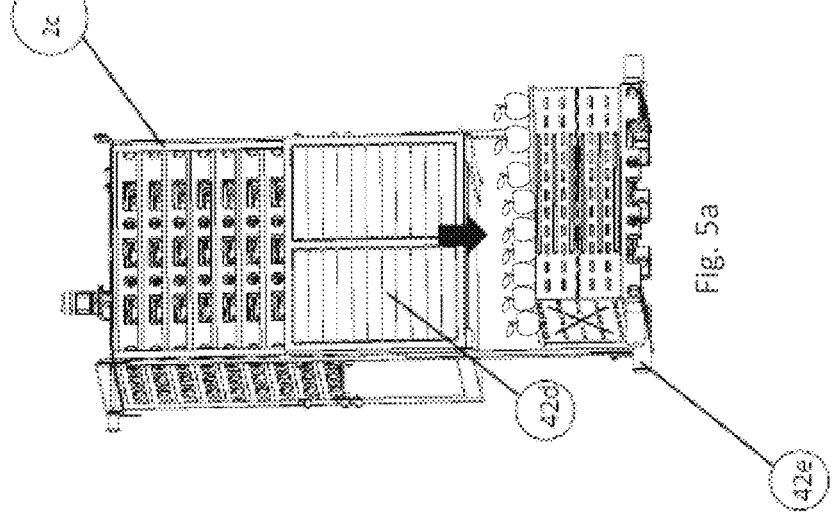

FIG. 5a demonstrates lifting a bin down to the ground and releasing it by activating holding pins 42e. FIG. 5b demonstrates unfolding a bin within its magazine. FIG. 5c demonstrates the movement of an open bin against the springs 42f of an elevator tray 42d unfolding the bin within its magazine.

FIG. 18a shows a side view of one configuration of a hybrid arm having 7 degrees of freedom needed to pick tree's fruits. The hybrid arm comprises a first transporting belt 7b mounted on a horizontal linear slider 7c and a gentle transporting belt 5b. A second transporting belt 7d comprises a robust servo joint enabling movement of this segment up or down according to the required height and further comprises a gentle transporting belt 5c. These two parts serve both the need of high moment of the arm and transporting of the harvested fruits. The shoulder of the high maneuverability robotic arm 7e is mounted on 7d. The arm elements 7e, 7f and 7g are mounted on 7d, and ensure reaching fruits behind stems within a tree 1 and aim to hold any detachable picking head 34a.

FIG. 18b presents a top view of the arm and its relations with the SPFCH-F. The hybrid arm can slide on the linear servo slider 7b and can be tilt also at joint of 7c. the vision means 27,28 are mounted on the forearm 7g.

FIG. 18c presents a zoom top view of a picking head that comprises 5-6 grabbing fingers 34d enabling picking 1-3 fruits at a time (similarly to a human hand). Optionally, it also comprises a cutting finger 35 comprising a cutting blade 35c, a blade protector 35e, a touch sensor 35f and a pin-type camera 27c mounted on the upper side of the blade's housing and aimed to sense the surface of the fruit in order to ensure exact cutting of the stem 1a, which is a crucial feature for some fruits, like citrus, which are puncturing each other, in the collecting bin, if the stem 1a is too long. FIG. 18d is a zoom view of a cutting finger in closed-mode of the blade protector. The positioning of the pin-type camera 27c is also shown. FIG. 18e presents an option of soft grabbing fingers for the same function.

The ability to grab two fruits at a time, as done by the human hand picking, is shown in FIGS. 22a-22e and 23a-23e or by a robotic hand as demonstrated in FIGS. 23d-23h. In this case a robotic hand 34a with five robotic fingers 34d is capable of grabbing two or even three apples (1b), holding and carrying them to a collecting catcher 5d.

Figure 27B:
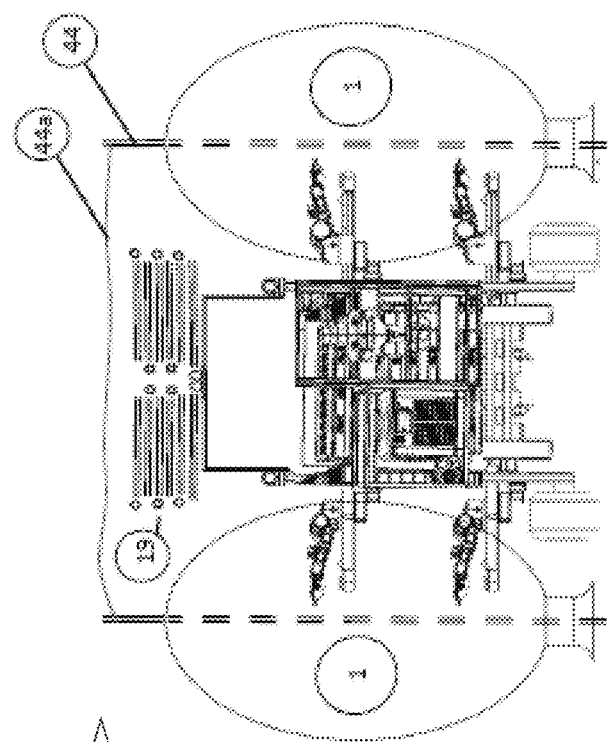
FIGS. 27a-27b are front views and illustrations of fruit harvesting while using solar panels for both electricity generation and as a protector against dazzle in front of the cameras.
Figure 27A:
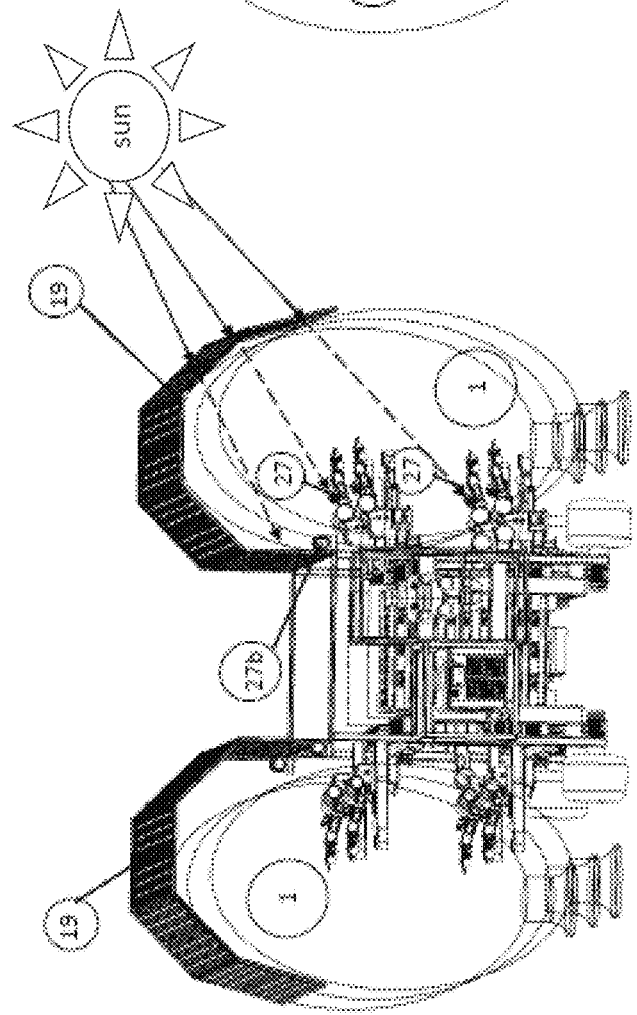

FIG. 27a illustrates harvesting orchard's fruits when solar panels are in use and when the sun dazzles the cameras 27,27B, such that it is necessary to protect from the dazzle at an acute angle (especially at sunrise and sunset) in order to produce good images. For such cases, in orchards that are not covered by upper shedding nets 44a held by pillar poles 44, an electric canopy outdoor sun shade shelter or other special arrangement of the flexible solar panels 19 may be used. The flexible and extendable solar panels 19 may be configured to automatically expend toward the direction of the sun, by hydraulic pistons or electrical motors, in order to produce solar energy and also to serve as a sun-protector against sun dazzle. In orchards covered by upper shedding nets 44a held by pillar poles 44, the solar panels will remain in folded configuration (FIG. 27b) or the nets may need to be fold into the pillar poles area prior to the harvesting time, to enable extending the solar panels.

REFERENCES

1) A Research for Intelligent Cotton Picking Robot Based on Machine Vision, Article—June 2008; DOI: 10.1109/ICINFA.2008.4608107
2) Yong Wang et al., "Object Recognition on Cotton Harvesting Robot Using Human Visual System", College of Science, PLA University of Science and Technology, 210003, Nanjing, China.
3) De-An et al., "Design and Control of an Apple Harvesting Robot", Biosystems Engineering, 2011, Vol. 110(2), pp. 112-122.
4) Cotton Pickers' Lament. http://www.britishpathe.com/video/the-cotton-pickers-lament.
5) Baeten et al., "Autonomous Fruit Picking Machine: A Robotic Apple Harvester", 6$^{th}$ International Conference on Field and Service Robotics-FSR 2007, 10 pages, Chamonix, France, July 2007.
6) U.S. Pat. No. 8,534,035.
7) U.S. Pat. No. 7,073,315.
8) CN 201135036Y.
9) CN 103503639B.
10) U.S. Pat. No. 5,768,869
11) U.S. Pat. No. 4,191,008
12) U.S. Pat. No. 4,519,193
13) US 2006/0213167
14) U.S. Pat. No. 3,606,750
15) U.S. Pat. No. 3,460,330
16) U.S. Pat. No. 9,475,189
17) U.S. Pat. No. 7,695,220
18) U.S. Pat. No. 7,882,686
19) Commercial YouTube publication: https://www.youtube.com/watch?v=UaL3UxUclKY

The invention claimed is:

1. A modular, human driven or autonomous/automatic self-propelled field crops harvester (SPFCH) device, for selective picking of crops, said device comprises:
  a. a detachable propelled carrier system of an automatic or self-propelled harvester comprising a propelled driving device and supporting mechanisms;
  b. a modular chassis, designed to be attached to said detachable propelled carrier system, said modular chassis comprises one or more modular, robotic hybrid harvesting arms, each arm comprises of: a proximal-end, a distal-end, and at least one robotic joint enabling vertical and horizontal movement, wherein:
    the proximal-end comprises a crop transporting mechanism designed to transport the harvested crop toward the SPFCH; and the distal-end comprises a picking head comprising: crop-identification optics; at least one sensor for sensing at least one of: proximity, rigidity, torque force for picking, size, color, shape, and brightness of the crop to be harvested; and a crop picking mechanism, said distal-end is designed to identify and harvest the crop and deliver same to the crop transporting mechanism of the proximal-end;

wherein:
the distal-end enables at least 2 or more degrees of maneuverability for better accessibility of the picking head to the crop within a tree environment;
said crop picking mechanism is selected from a gripper and a suction, or a combination thereof, and
each one of said robotic hybrid harvesting arms is adapted for vertical, horizontal and back and forth movements for accessing the crop and deliver same to a crop collecting catcher;

c. a computing system comprising a processor and a memory adapted for: receiving data from said crop-identification optics; detecting crop to be harvested and potential contaminants; and operating all the robotic harvesting arms;

d. one or more modular horizontal or vertical boom, each modular boom comprising secured hanging points to mount said at least one or more modular robotic arms selected according to the crop being harvested, each secured hanging point comprises electricity connectors, and identification based data connections;

e. a container for collecting the harvested crop;

f. a main conveyor for transporting the harvested crop from each harvesting arm or boom into said container;

g. an automatic container replacer when said container is full;

h. a magazine holding foldable containers designed to automatically open/unfold said foldable containers whenever a container is filled and replaced; and i. an automatic conveying system for emptying the harvested crop from the SPFCH;

wherein said computing system controls:
navigation of the SPFCH;
a movement speed of the SPFCH during harvesting;
each one of the harvesting arms according to data obtained from said crop-identification optics, the type of crop being harvested, and a selected harvesting-algorithm; and
each one of the crop picking mechanism, according to signals obtained from said sensors or optics.

2. The SPFCH device of claim 1, further comprising at least one of:
a packing unit for packing the harvested crop;
an unfolding mechanism for unfolding said folded containers;
a crane to pile containers of crop or bales of crop on top of each other and to efficiently order them on a collecting platform;
foldable or extendable solar panels for recharging a rechargeable power source or for directly operating the SPFCH when day light is available and for protecting against dazzle at an acute angle, and a central electric circuit that manages the electricity generated by said solar panels and synchronizes them with the main electrical system of the SPFCH and its motored generator; or
a navigation system comprising GPS or guiding sensors, for controlling/navigating the SPFCH on roads or within a field to be harvested and while harvesting.

3. The SPFCH device of claim 1, wherein each one of said at least one modular horizontal or vertical booms further comprises pre-designed safety hanger points with connectors for electricity, communication and air/oil pressure which works independently regardless the boom's mounting position.

4. The SPFCH device of claim 1, wherein said computer uses data obtained from said crop-identification optics to automatically recognize the ready for picking one or more crops within a crop's cluster by using an algorithm according to the type of crop being harvested; instructs the harvesting arms to pick the one or more crops within the crop's cluster, and transport the harvested crop to the main conveyor that transfers the crop to said container.

5. The SPFCH device of claim 1, wherein said crop picking mechanism is a gripper, and each harvesting robotic arm further comprises a cutting tool to cut a crop's holding stem while grabbing the crop without the need of second tool for cutting.

6. The SPFCH device of claim 5, wherein said gripper is a hand picking tool having 4-7 fingers.

7. The SPFCH device of claim 1, wherein said crop is light and the picking mechanism is vacuum and each harvesting robotic arm further comprises a hose connected to a local or main vacuum generator.

8. The SPFCH device of claim 7, wherein said crop picking mechanism further comprises a gripper.

9. The SPFCH device of claim 1, wherein said crop is not cotton, and each robotic harvesting arm comprises: (i) a gripper mechanism designed to gently grip said crop and transfer the harvested crop to said crop transporting mechanism mounted on the harvesting arm and the boom; and (ii) an automatic cutting mechanism designed to cut the crop's stem.

10. The SPFCH device of claim 9, wherein said gripper mechanism is a hand picking tool having 4-7 fingers.

11. The SPFCH device of claim 1, wherein said crop is cotton, and said SPFCH further comprises: (i) one or more vacuum generating units connected to a vacuum hose located on each one of said harvesting arms; (ii) one or more ginning units, for separating cotton lint from the seeds; (iii) temperature controlled heated conveyors, ducts or tubes, for delivering and feeding the harvested seed-cotton from the booms to a ginning feeder hopper of said ginning units while drying the seed-cotton before ginning; (iv) a bale press for pressing the seed-free cotton lint into bales, and a conveyer for transporting ready bales to a collecting trailer platform or to a tail hydraulic lift platform; and (v) a cotton seeds' container.

12. The SPFCH device of claim 11, wherein said heated conveyors, ducts or tubes comprise partitions mounted as labyrinth, aimed to increase the length of said conveyor, tube or duct.

13. The SPFCH device of claim 11, further comprising at least one of:
a controlled heating unit for heating said heated conveyers, ducts or tubes;
a spiral or conveying mechanism for emptying the cotton seeds' container or the bale's platform to enable continued harvesting; or
a sampling device designed to obtain a sample from every bale for assessing quality of the lint/fibers.

14. A process of harvesting row crops comprising the steps of:
a) attaching the modular chassis as defined in claim 1 to the detachable propelled carrier system as defined in claim 1 to obtain the SPFCH device of claim 1;

b) activating said SPFCH device thereby enabling it to harvest automatically while:
  recognizing ready-for-harvest crop as well as various contaminations;
  picking desired crop only, while avoiding picking said contaminants;
  transferring the harvested crop by said crop transporting mechanism and said main conveyor; and
  emptying or transferring the container filled with the harvested crop to an accompanying wagon or truck, or to the ground.

15. The process of claim 14 further comprising at least one of the following steps: (i) prior to step (a), assembling onto the booms harvesting robotic arms according to the crop to be harvested; (ii) adjusting the amount and position of the harvesting robotic arms on each boom according to the field and crop to be harvested; (iii) guiding manually or automatically the harvester by sensors or GPS; and (iv) sampling every container or a bale of crop for assessing quality control.

16. The process of claim 14, wherein said crop is cotton, and said SPFCH further comprises: (i) one or more vacuum generating units connected to a vacuum hose located on each one of said harvesting arms; (ii) one or more ginning units, for separating cotton lint from the seeds; (iii) temperature controlled heated conveyors, ducts or tubes, for delivering and feeding the harvested seed-cotton from the booms to a ginning feeder hopper of said ginning units while controlling the drying of the seed-cotton before ginning; (iv) a bale press for pressing the seed-free cotton lint into bales, and a conveyer for transporting ready bales to a collecting trailer platform or to a flat tail hydraulic lift platform; and (v) cotton seeds' container, wherein said process further comprises the following steps:

harvesting the cotton by vacuum only or by a combination of pinching and vacuum, while avoiding picking possible contamination, and transporting same to the ginning unit while heat-drying the harvested seed-cotton;
ginning the seed-cotton to separate cotton lint fibers from cotton seeds;
controlling the ginning speed and capacity;
transporting the cotton lint to the bale press and creating cotton bales;
transporting said cotton bales to a trailed platform or a flat hydraulic tail lift;
accumulating the separated cotton seeds in a seeds' container; and
unloading the seeds from the container and the bales from the platform out of the SPCFH to enable continuance harvesting.

17. The process of claim 16, further comprising a step of grabbing at least two lint samples from each bale for quality control.

18. The process of claim 14, wherein said crop is not cotton, and each hybrid robotic harvesting arm of said SPFCH further comprises: (i) a gripper mechanism designed to gently grip the crop and transfer the harvested crop to the crop transporting mechanism mounted on the boom; and (iii) an automatic cutting mechanism designed to cut the crop's connecting stem, wherein said process further comprises the stop of harvesting the crop by gripping only the crop to be harvested with said gripper mechanism and cutting the stem, when needed, with said automatic cutting mechanism.

19. The process of claim 18, wherein said process further comprises a step of transporting a full container to the ground.

* * * * *

UNITED STATES PATENT AND TRADEMARK OFFICE
CERTIFICATE OF CORRECTION

PATENT NO. : 11,533,850 B2
APPLICATION NO. : 16/644476
DATED : December 27, 2022
INVENTOR(S) : Uzi Mor Page 1 of 1

It is certified that error appears in the above-identified patent and that said Letters Patent is hereby corrected as shown below:

On the Title Page

In the abstract:

Column 2, Line 7, delete "orchards" and insert --orchard's.--

Column 2, Line 10, delete "a an" and insert --an.--

In the Claims

Column 36, Line 15, in Claim 16, delete "SPCFH" and insert --SPFCH.--

Column 36, Line 24, in Claim 18, delete "(iii)" and insert --(ii).--

Column 36, Line 27, in Claim 18, delete "stop" and insert --step.--

Signed and Sealed this
Twenty-fourth Day of September, 2024

Katherine Kelly Vidal
*Director of the United States Patent and Trademark Office*